US 8,868,147 B2

United States Patent
Stippick et al.

(10) Patent No.: US 8,868,147 B2
(45) Date of Patent: Oct. 21, 2014

(54) METHOD AND APPARATUS FOR CONTROLLING POSITIONING OF A NONINVASIVE ANALYZER SAMPLE PROBE

(75) Inventors: Timothy W. Stippick, Phoenix, AZ (US); Thomas B. Blank, Gilbert, AZ (US); Timothy L. Ruchti, Gurnee, IL (US); Christopher Slawinski, Mesa, AZ (US)

(73) Assignee: GLT Acquisition Corp., Irvine, CA (US)

( * ) Notice: Subject to any disclaimer, the term of this patent is extended or adjusted under 35 U.S.C. 154(b) by 1694 days.

(21) Appl. No.: 12/125,017

(22) Filed: May 21, 2008

(65) Prior Publication Data

US 2008/0319299 A1 Dec. 25, 2008

Related U.S. Application Data

(63) Continuation-in-part of application No. 11/625,752, filed on Jan. 22, 2007, now abandoned, which is a continuation-in-part of application No. 11/117,104, filed on Apr. 27, 2005, now Pat. No. 7,519,406, which is a continuation-in-part of application No. PCT/US2007/083497, filed on Nov. 2, 2007.

(60) Provisional application No. 60/864,375, filed on Nov. 3, 2006, provisional application No. 60/943,495, filed on Jun. 12, 2007, provisional application No. 60/566,568, filed on Apr. 28, 2004.

(51) Int. Cl.
*A61B 5/1455* (2006.01)
*A61B 5/06* (2006.01)
*A61B 5/145* (2006.01)
*A61B 5/00* (2006.01)

(52) U.S. Cl.
CPC .............. *A61B 5/1455* (2013.01); *A61B 5/061* (2013.01); *A61B 5/14532* (2013.01); *A61B 5/14546* (2013.01); *A61B 5/6843* (2013.01)
USPC ............ 600/310; 600/316; 600/322; 600/344

(58) Field of Classification Search
USPC .................................................. 600/309–476
See application file for complete search history.

(56) References Cited

U.S. PATENT DOCUMENTS 4,033,054 A 7/1977 Fukuoka
4,213,462 A 7/1980 Sato (Continued)

FOREIGN PATENT DOCUMENTS

CN 1214768 4/1999
DE 2640987 3/1978

(Continued)

OTHER PUBLICATIONS

Webster's II New Riverside University Dictionary: The Riverside Publishing Company, 1994, p. 1000.

(Continued)

*Primary Examiner* — Eric Winakur
*Assistant Examiner* — Marjan Fardanesh
(74) *Attorney, Agent, or Firm* — Knobbe, Martens, Olson & Bear, LLP

(57) ABSTRACT

The invention relates generally to a probe interface method and apparatus for use in conjunction with an optical based noninvasive analyzer. More particularly, an algorithm controls a sample probe position and attitude relative to a skin sample site before and/or during sampling. For example, a sample probe head of a sample module is controlled by an algorithm along the normal-to-skin-axis. Preferably, the sample probe head is positioned in terms of 3-D location in the x-, y-, and z-axes and is attitude orientated in terms of pitch, yaw, and roll. Further, attitude of the probe head is preferably orientated prior to contact of the sample probe head with the tissue sample using indicators, such as non-contact distance feedback from capacitance sensor, contacting or non-contacting optical sensors, and/or contact electrical sensors.

23 Claims, 14 Drawing Sheets

(56) References Cited

U.S. PATENT DOCUMENTS

| | | |
|---|---|---|
| 4,272,040 A | 6/1981 | Bastian et al. |
| 4,321,930 A | 3/1982 | Jobsis |
| 4,548,505 A | 10/1985 | Ono |
| 4,674,338 A | 6/1987 | Carpenter |
| 4,685,464 A | 8/1987 | Goldberger et al. |
| 4,798,955 A | 1/1989 | Rosenthal |
| 4,830,014 A | 5/1989 | Goodman et al. |
| 4,866,644 A | 9/1989 | Shenk et al. |
| 4,882,492 A | 11/1989 | Schlager |
| 5,007,423 A | 4/1991 | Branstetter et al. |
| 5,068,536 A | 11/1991 | Rosenthal |
| 5,070,874 A | 12/1991 | Barnes et al. |
| 5,131,391 A | 7/1992 | Sakai et al. |
| 5,170,786 A | 12/1992 | Thomas |
| 5,285,783 A | 2/1994 | Secker |
| 5,299,570 A | 4/1994 | Hatschek |
| 5,348,003 A | 9/1994 | Caro |
| 5,361,758 A | 11/1994 | Hall et al. |
| 5,398,681 A | 3/1995 | Kupershmidt |
| 5,448,662 A | 9/1995 | Kittell |
| 5,492,118 A | 2/1996 | Gratton |
| 5,506,482 A | 4/1996 | Teramatsu |
| 5,507,288 A | 4/1996 | Bocker et al. |
| 5,517,301 A | 5/1996 | Dave |
| 5,548,674 A | 8/1996 | Rondeau |
| 5,574,855 A | 11/1996 | Rosich et al. |
| 5,596,987 A | 1/1997 | Chance |
| 5,619,195 A | 4/1997 | Allen |
| 5,632,273 A | 5/1997 | Suzuki |
| 5,636,634 A | 6/1997 | Kordis |
| 5,655,530 A | 8/1997 | Messerschmidt |
| 5,661,843 A | 8/1997 | Rickenbach |
| 5,671,317 A | 9/1997 | Weishaupt |
| 5,687,717 A | 11/1997 | Halpern et al. |
| 5,725,480 A | 3/1998 | Ooste |
| 5,730,140 A | 3/1998 | Fitch |
| 5,747,806 A | 5/1998 | Khalil et al. |
| 5,750,994 A | 5/1998 | Schlager |
| 5,769,076 A | 6/1998 | Maekawa |
| 5,770,454 A | 6/1998 | Essenpreis et al. |
| 5,823,951 A | 10/1998 | Messerschmidt |
| 5,825,488 A | 10/1998 | Kohl et al. |
| 5,830,132 A | 11/1998 | Robinson |
| 5,869,075 A | 2/1999 | Krzysik |
| 5,877,664 A | 3/1999 | Jackson, Jr. |
| 5,879,373 A | 3/1999 | Roper et al. |
| 5,891,021 A | 4/1999 | Dillon |
| 5,912,656 A | 6/1999 | Tham et al. |
| 5,935,062 A | 8/1999 | Messerschmidt et al. |
| 5,945,676 A | 8/1999 | Khalil et al. |
| 5,956,150 A | 9/1999 | Kanne |
| 5,978,691 A | 11/1999 | Mills |
| 6,014,756 A | 1/2000 | Dottling |
| 6,040,578 A | 3/2000 | Malin et al. |
| 6,045,511 A | 4/2000 | Ott |
| 6,067,463 A | 5/2000 | Jeng et al. |
| 6,088,605 A | 7/2000 | Griffith et al. |
| 6,093,156 A | 7/2000 | Cunningham et al. |
| 6,095,974 A | 8/2000 | Shemwell et al. |
| 6,115,673 A | 9/2000 | Malin et al. |
| 6,144,868 A | 11/2000 | Parker |
| 6,147,749 A | 11/2000 | Kubo et al. |
| 6,152,876 A | 11/2000 | Robinson |
| 6,157,041 A | 12/2000 | Thomas et al. |
| 6,180,416 B1 | 1/2001 | Kuenik et al. |
| 6,230,034 B1 | 5/2001 | Messerschmidt |
| 6,233,471 B1 | 5/2001 | Berner et al. |
| 6,236,047 B1 | 5/2001 | Malin et al. |
| 6,240,306 B1 | 5/2001 | Rohrsheib et al. |
| 6,253,097 B1 | 6/2001 | Aronow et al. |
| 6,272,364 B1 | 8/2001 | Kurnik |
| 6,280,381 B1 | 8/2001 | Malin et al. |
| 6,289,230 B1 | 9/2001 | Chaiken et al. |
| 6,304,766 B1 | 10/2001 | Colvin, Jr. |
| 6,326,160 B1 | 12/2001 | Dunn et al. |
| 6,330,464 B1 | 12/2001 | Colvin, Jr. et al. |
| 6,334,360 B1 | 1/2002 | Chen |
| 6,381,489 B1 | 4/2002 | Ashibe |
| 6,400,974 B1 | 6/2002 | Lesho |
| 6,405,065 B1 | 6/2002 | Malin et al. |
| 6,411,373 B1 | 6/2002 | Garside et al. |
| 6,411,838 B1 | 6/2002 | Nordstrom et al. |
| 6,415,167 B1 | 7/2002 | Blank et al. |
| 6,421,549 B1 | 7/2002 | Jacques |
| 6,441,388 B1 | 8/2002 | Thomas |
| 6,442,408 B1 | 8/2002 | Wenzel et al. |
| 6,449,500 B1 | 9/2002 | Asai et al. |
| 6,456,870 B1 | 9/2002 | Rennert et al. |
| 6,475,800 B1 | 11/2002 | Hazen et al. |
| 6,487,429 B2 | 11/2002 | Hockersmith et al. |
| 6,493,566 B1 | 12/2002 | Ruchti et al. |
| 6,501,982 B1 | 12/2002 | Ruchti et al. |
| 6,507,687 B1 | 1/2003 | Juskaitis et al. |
| 6,512,937 B2 | 1/2003 | Blank et al. |
| 6,512,982 B2 | 1/2003 | Yang et al. |
| 6,528,809 B1 | 3/2003 | Thomas |
| 6,546,269 B1 | 4/2003 | Kurnik |
| 6,558,320 B1 | 5/2003 | Causey et al. |
| 6,574,490 B2 | 6/2003 | Abbink et al. |
| 6,582,381 B1 * | 6/2003 | Yehezkeli et al. ................. 601/2 |
| 6,585,370 B2 | 7/2003 | Zelman |
| 6,631,282 B2 | 10/2003 | Rule et al. |
| 6,641,533 B2 | 11/2003 | Causey, III et al. |
| 6,690,958 B1 | 2/2004 | Walker et al. |
| 6,788,965 B2 | 9/2004 | Ruchti |
| 6,839,583 B1 | 1/2005 | Lewandowski et al. |
| 6,920,345 B2 | 7/2005 | Al-Ali et al. |
| 6,927,843 B2 | 8/2005 | Dick |
| 7,133,710 B2 | 11/2006 | Acosta et al. |
| 7,178,063 B1 | 2/2007 | Smith |
| 7,409,330 B2 | 8/2008 | Kumamoto |
| 2002/0026106 A1 | 2/2002 | Khalil et al. |
| 2002/0058864 A1 | 5/2002 | Mansfield |
| 2002/0087949 A1 | 7/2002 | Golender et al. |
| 2003/0040663 A1 | 2/2003 | Rule |
| 2003/0156270 A1 | 8/2003 | Hunter |
| 2003/0208113 A1 | 11/2003 | Mault et al. |
| 2003/0216627 A1 | 11/2003 | Lorenz |
| 2003/0216630 A1 | 11/2003 | Jersey-Willuhn et al. |
| 2004/0068163 A1 | 4/2004 | Ruchti |
| 2004/0077937 A1 | 4/2004 | Yarden |
| 2004/0127777 A1 | 7/2004 | Ruchti |
| 2004/0163032 A1 | 8/2004 | Guo |
| 2004/0167473 A1 | 8/2004 | Moenning |
| 2005/0007125 A1 | 1/2005 | Heger |
| 2005/0034102 A1 | 2/2005 | Peck |
| 2005/0054908 A1 | 3/2005 | Blank et al. |
| 2005/0187439 A1 | 8/2005 | Blank et al. |
| 2005/0267342 A1 | 12/2005 | Blank et al. |
| 2006/0200017 A1 | 9/2006 | Monfre et al. |
| 2006/0211931 A1 | 9/2006 | Blank et al. |
| 2006/0217602 A1 | 9/2006 | Abul-haj et al. |
| 2008/0009835 A1 | 1/2008 | Kriesel et al. |
| 2008/0033275 A1 | 2/2008 | Blank et al. |
| 2009/0062635 A1 | 3/2009 | Brauker et al. |

FOREIGN PATENT DOCUMENTS

| | | |
|---|---|---|
| EP | 1254631 | 11/2002 |
| JP | 04-215742 | 8/1992 |
| JP | 05-317295 | 12/1993 |
| JP | 08-215180 | 8/1996 |
| JP | 2001-037741 | 2/2001 |
| JP | 2001-299727 | 10/2001 |
| JP | 2002535023 | 10/2002 |
| WO | WO 96/28084 | 9/1996 |
| WO | WO 97/05819 | 2/1997 |
| WO | WO 97/28437 | 8/1997 |
| WO | WO 00/22982 | 4/2000 |
| WO | WO 00/42907 | 7/2000 |
| WO | WO 00/74562 | 12/2000 |
| WO | WO 00/76575 A3 | 12/2000 |
| WO | WO 01/31304 | 5/2001 |

(56) References Cited

FOREIGN PATENT DOCUMENTS

| WO | WO 01/58355 | 8/2001 |
|---|---|---|
| WO | WO 01/72222 | 10/2001 |
| WO | WO 01/82794 | 11/2001 |

OTHER PUBLICATIONS

Diabetes Statistics. Bethesda, MD: National Institute of Health, Publication No. 98-3926, Nov. 1997.

The Diabetes Control and Complications Trial Research Group. "The effect of intensive treatment of diabetes on the development and progression of long-term complications in insulin-dependent diabetes mellitus." N Eng J of Med 1993;329:977-86.

U.K. Prospective Diabetes Study (UKPDS) Group, "Intensive blood-glucose control with sulphonylureas or insulin compared with conventional treatment and risk of complications in patients with type 2 diabetes," *Lancet*, vol. 352, pp. 837-853, 1998.

Ohkubo, Y., H. Kishikawa, E. Araki, T. Miyata, S. Isami, S. Motoyoshi, Y. Kojima, N. Furuyoshi, and M. Shichizi, "Intensive insulin therapy prevents the progression of diabetic microvascular complications in Japanese patients with non-insulin-dependent diabetes mellitus: a randomized prospective 6-year study," *Diabetes Res Clin Pract*, vol. 28, pp. 103-117, 1995.

Savitzky, A. and M. J. E. Golay. "Smoothing and Differentiation of Data by Simplified Least Squares Procedures," Anal. Chem., vol. 36, No. 8, pp. 1627-1639, 1964.

Hazen, Kevin H. Glucose Determination in Biological Matrices Using Near-Infrared Spectr Sage, Burton H. "FDA Panel Approves Cygnus's Noninvasive GlucoWatch™ ", *Diabetes Technology & Therapeutics*, 2, 2000, 115-116.oscopy, doctoral dissertation, University of Iowa, 1995.

Tamada, J.A., S. Garg, L. Jovanovic, K.R. Pitzer, S. Fermi, R.O. Potts, "Noninvasive Glucose Monitoring Comprehensive Cinical Results,"*JAMA*, vol. 282, No. 19, pp. 1839-1844, Nov. 17, 1999.

"GlucoWatch Automatic Glucose Biographer and AutoSensors", Cygnus Inc., Document #199200, Rev. Mar. 2001.

Trajanoski, Zlatko; Brunner, Gernot A.; Schaupp, Lucas; Ellmerer, Martin; Wach, Paul; Pieber, Thomas R.; Kotanko, Peter; Skrabai, Falko "Open-Flow Microperfusion of Subcutaneous Adipose Tissue for ON-Line Continuous Ex Vivo Measurement of Glucose Concentration", *Diabetes Care*, 20, 1997, 1114-1120.

Trajanoski, Zlatko; Wach, Paul; Gfrerer, Robert "Portable Device for Continuous Fractionated Blood Sampling and Continuous ex vivo Blood Glucose Monitoring", *Biosensors and Bioelectronics*, 11, 1996, 479-487.

Gross, Todd M.; Bode, Bruce W.; Einhorn, Daniel; Kayne, David M.; Reed, John H.; White, Neil H.; Mastrototaro, John J. "Performance Evaluation of the MiniMed Continuous Glucose Monitoring System During Patient Home Use", *Diabetes Technology & Therapeutics*, 2, 2000, 49-56.

Rebrin, Kerstin; Steil, Gary M.; Antwerp, William P. Van; Mastrototaro, John J. "Subcutaneous Glucose Predicts Plasma Glucose Independent of Insulin: Implications for Continuous Monitoring", *Am., J. Physiol.*, 277, 1999, E561-E571, 0193-1849/99, The American Physiological Society, 1999.

Geladi, P., D. McDougall and H. Martens. "Linearization and Scatter-Correction for Near-Infrared Reflectance Spectra of Meat," *Applied Spectroscopy*, vol. 39, pp. 491-500, 1985.

R.J. Barnes, M.S. Dhanoa, and S. Lister, Standard Normal Variate Transformation and De-trending of Near-Infrared Diffuse Reflectance Spectra, *Applied Spectroscopy*, 43, pp. 772-777, 1989.

T. Isaksson and B. R. Kowalski, "Piece-Wise Multiplicative Scatter Correction Applied to Near-Infrared Diffuse Transmittance Data From Meat Products", *Applied Spectroscopy*, 47, pp. 702-709, 1993.

H. Martens and E. Stark, "Extended multiplicative signal correction and spectral interference subtraction: new preprocessing methods for near infrared spectroscopy", *J. Pharm Biomed Anal*, 9, pp. 625-635, 1991.

T. Isaksson, Z. Wang, and B. R. Kowalski, Optimised scaling (OS-2) regression applied to near infrared . . . food products, *J. Near Infrared Spectroscopy*, 1, pp. 85-97, 1993.

Sum, S.T., "Spectral Signal Correction for Multivariate Calibration," Doctoral Disseration, University of Delaware, Summer 1998.

Sum, S.T. and S.D. Brown, "Standardization of Fiber-Optic Probes for Near-Infrared Multivariate Calibrations," *Applied Spectroscopy*, vol. 52, No. 6, pp. 869-877, 1998.

T. B. Blank, S.T. Sum, S.D. Brown and S.L. Monfre, "Transfer of near-infrared multivariate calibrations without standards," *Analytical Chemistry*, 68, pp. 2987-2995, 1996.

Oppenheim, Alan V. and R. W. Schafer, *Digital Signal Processing*, Englewood Cliffs, NJ: Prentice Hall, 1975, pp. 195-271.

Otto, M., Statistics and Computer Application in Analytical Chemistry; *Chemometrics*, Weinheim: Wiley-VCH, 1999.

Beebe, K.R., R.J. Pell and M.B. Seasholtz, *Chemometrics A Practical Guide*, New York: John Wiley & Sons, Inc., 1998.

M.A. Sharaf, D.L. Illman and B.R. Kowalski, *Chemometrics*, New York: John Wiley & Sons, Inc., 1996.

Massart, et al.; *Data Handling in Scinece and Technology*—vol. 2; Chemometrics: a textbook; 1988 Elsevier Science Publishing Co., Inc. pp. 215-253.

\* cited by examiner

Time 1

Time 2

Time 1

Time 2

METHOD AND APPARATUS FOR CONTROLLING POSITIONING OF A NONINVASIVE ANALYZER SAMPLE PROBE

CROSS REFERENCE TO RELATED APPLICATIONS

This application:
claims benefit of U.S. Provisional Application No. 60/943,495 filed Jun. 12, 2007;
is a continuation-in-part of U.S. patent application Ser. No. 11/625,752 filed Jan. 22, 2007, which is a continuation-in-part of U.S. patent application Ser. No. 11/117,104, filed Apr. 27, 2005, which claims the benefit of U.S. provisional application No. 60/566,568, filed Apr. 28, 2004; and
is a continuation-in-part of PCT application No. PCT/US07/83497 filed Nov. 2, 2007, which claims benefit of U.S. provisional patent application no. 60/864,375 filed Nov. 3, 2006, all of which are incorporated herein in their entirety by this reference thereto.

BACKGROUND OF THE INVENTION

1. Field of the Invention

The invention relates generally to measurement of analyte properties in tissue. One embodiment relates to sample probe movement control in a noninvasive measurement.

2. Discussion of the Related Art

Sampling deformable skin tissue with a spectrometer is complicated by optical and mechanical mechanisms occurring before and/or during sampling.

In a first case, a representative optical sample of an object is collected without contacting the object with the spectrometer. In this case, specular reflectance and stray light is of concern. In one instance, mechano-optical methods are used to reduce the amount of specularly reflected light collected. However, this is greatly complicated by an object having a surface that diffusely scatters light. In a second instance, an algorithm is used to reduce the effects of specular reflectance. This is complicated by specularly reflected light contributing in an additive manner to the resultant spectrum. The additive contribution results in a nonlinear interference, which results in a distortion of the spectrum that is difficult to remove. The problem is greatly enhanced as the magnitude of the analyte signal decreases. Thus, for low signal-to-noise ratio measurements, specularly reflected light is preferably avoided. For example, noninvasively determining an analyte property, such as glucose concentration, from a spectrum of the body is complicated by additive specularly reflected light in the collected spectrum. As the analyte signal decreases in magnitude, the impact of specularly reflected light increases.

In a second case, a spectrum of an object is collected after contacting the object with a spectrometer. For objects or samples that are deformable, the optical properties of the sample are changed due to contact of an optical probe with the sample, which deforms the sample and results in changed optical properties of the sample. Changed optical properties due to movement of a sample before or during sampling include:
absorbance; and
scattering.

In this second case, the sampling method alters the sample, often detrimentally. The changes in the sample resulting from the sampling method degrade resulting sample interpretation. As the signal level of the analyte decreases, the relative changes in the sample due to sampling result in increasing difficulty in extraction of analyte signal. In some instances, the sampling induced changes preclude precise and/or accurate analyte property determination from a sample spectrum. For example, a sample probe contacting skin of a human alters the sample. Changes to the skin sample upon contact, during sampling, and/or before sampling include:
stretching of skin;
compression of skin; and
altered spatial distribution of sample constituents.

Further, the changes are often time dependent and methodology of sampling dependent. Typically, the degree of contact to the sample by the spectrometer results in nonlinear changes to a resulting collected spectrum.

Manually manipulating a spectrometer during the method of optical sampling requires human interaction. Humans are limited in terms of dexterity, precision, reproducibility, and sight. For example, placing a spectrometer in contact with an object during sampling is complicated by a number of parameters including any of:
not being able to reach and see the sample at the same time;
the actual sampling area being visually obscured by part of the spectrometer or sample;
placing the analyzer relative to the sample within precision and/or accuracy specifications at, near, or beyond human control limits; and
repeatedly making a measurement due to human fatigue and frailty.

Noninvasive Technologies

There are a number of reports on noninvasive technologies. Some of these relate to general instrumentation configurations, such as those required for noninvasive glucose concentration estimation, while others refer to sampling technologies. Those related to the present invention are briefly reviewed here:

P. Rolfe, Investigating substances in a patient's bloodstream, U.K. patent application ser. no. 2,033,575 (Aug. 24, 1979) describes an apparatus for directing light into the body, detecting attenuated backscattered light, and using the collected signal to determine glucose concentrations in or near the bloodstream.

C. Dahne, D. Gross, Spectrophotometric method and apparatus for the non-invasive, U.S. Pat. No. 4,655,225 (Apr. 7, 1987) describe a method and apparatus for directing light into a patient's body, collecting transmitted or backscattered light, and determining glucose concentrations from selected near-infrared wavelength bands. Wavelengths include 1560 to 1590, 1750 to 1780, 2085 to 2115, and 2255 to 2285 nm with at least one additional reference signal from 1000 to 2700 nm.

R. Barnes, J. Brasch, D. Purdy, W. Lougheed, Non-invasive determination of analyte concentration in body of mammals, U.S. Pat. No. 5,379,764 (Jan. 10, 1995) describe a noninvasive glucose concentration estimation analyzer that uses data pretreatment in conjunction with a multivariate analysis to estimate blood glucose concentrations.

M. Robinson., K. Ward, R. Eaton, D. Haaland, Method and apparatus for determining the similarity of a biological analyte from a model constructed from known biological fluids, U.S. Pat. No. 4,975,581 (Dec. 4, 1990) describe a method and apparatus for measuring a concentration of a biological analyte, such as glucose concentration, using infrared spectroscopy in conjunction with a multivariate model. The multivariate model is constructed from a plurality of known biological fluid samples.

J. Hall, T. Cadell, Method and device for measuring concentration levels of blood constituents non-invasively, U.S. Pat. No. 5,361,758 (Nov. 8, 1994) describe a noninvasive device and method for determining analyte concentrations within a living subject using polychromatic light, a wavelength separation device, and an array detector. The apparatus uses a receptor shaped to accept a fingertip with means for blocking extraneous light.

S. Malin, G Khalil, Method and apparatus for multi-spectral analysis of organic blood analytes in noninvasive infrared spectroscopy, U.S. Pat. No. 6,040,578 (Mar. 21, 2000) describe a method and apparatus for determination of an organic blood analyte using multi-spectral analysis in the near-infrared. A plurality of distinct nonoverlapping regions of wavelengths are incident upon a sample surface, diffusely reflected radiation is collected, and the analyte concentration is determined via chemometric techniques.

Specular Reflectance

R. Messerschmidt, D. Sting Blocker device for eliminating specular reflectance from a diffuse reflectance spectrum, U.S. Pat. No. 4,661,706 (Apr. 28, 1987) describe a reduction of specular reflectance by a mechanical device. A blade-like device "skims" the specular light before it impinges on the detector. A disadvantage of this system is that it does not efficiently collect diffusely reflected light and the alignment is problematic.

R. Messerschmidt, M. Robinson Diffuse reflectance monitoring apparatus, U.S. Pat. No. 5,636,633 (Jun. 10, 1997) describe a specular control device for diffuse reflectance spectroscopy using a group of reflecting and open sections.

R. Messerschmidt, M. Robinson Diffuse reflectance monitoring apparatus, U.S. Pat. No. 5,935,062 (Aug. 10, 1999) and R. Messerschmidt, M. Robinson Diffuse reflectance monitoring apparatus, U.S. Pat. No. 6,230,034 (May 8, 2001) describe a diffuse reflectance control device that discriminates between diffusely reflected light that is reflected from selected depths. This control device additionally acts as a blocker to prevent specularly reflected light from reaching the detector.

Malin, supra, describes the use of specularly reflected light in regions of high water absorbance, such as 1450 and 1900 nm, to mark the presence of outlier spectra wherein the specularly reflected light is not sufficiently reduced.

K. Hazen, G. Acosta, A. Abul-Haj, R. Abul-Haj, Apparatus and method for reproducibly modifying localized absorption and scattering coefficients at a tissue measurement site during optical sampling, U.S. Pat. No. 6,534,012 (Mar. 18, 2003) describe a mechanical device for applying sufficient and reproducible contact of the apparatus to the sampling medium to minimize specular reflectance. Further, the apparatus allows for reproducible applied pressure to the sample site and reproducible temperature at the sample site.

Temperature

K. Hazen, Glucose Determination in Biological Matrices Using Near-Infrared Spectroscopy, doctoral dissertation, University of Iowa (1995) describes the adverse effect of temperature on near-infrared based glucose concentration estimations. Physiological constituents have near-infrared absorbance spectra that are sensitive, in terms of magnitude and location, to localized temperature and the sensitivity impacts noninvasive glucose concentration estimation.

Pressure

E. Chan, B. Sorg, D. Protsenko, M. O'Neil, M. Motamedi, A. Welch, Effects of compression on soft tissue optical properties, IEEE Journal of Selected Topics in Quantum Electronics, Vol. 2, no. 4, pp. 943-950 (1996) describe the effect of pressure on absorption and reduced scattering coefficients from 400 to 1800 nm. Most specimens show an increase in the scattering coefficient with compression.

K. Hazen, G. Acosta, A. Abul-Haj, R. Abul-Haj, Apparatus and method for reproducibly modifying localized absorption and scattering coefficients at a tissue measurement site during optical sampling, U.S. Pat. No. 6,534,012 (Mar. 18, 2003) describe in a first embodiment a noninvasive glucose concentration estimation apparatus for either varying the pressure applied to a sample site or maintaining a constant pressure on a sample site in a controlled and reproducible manner by moving a sample probe along the z-axis perpendicular to the sample site surface. In an additional described embodiment, the arm sample site platform is moved along the z-axis that is perpendicular to the plane defined by the sample surface by raising or lowering the sample holder platform relative to the analyzer probe tip. The '012 patent further teaches proper contact to be the moment specularly reflected light is about zero at the water bands about 1950 and 2500 nm.

Coupling Fluid

A number of sources describe coupling fluids with important sampling parameters.

Index of refraction matching between the sampling apparatus and sampled medium to enhance optical throughput is known. Glycerol is a common index matching fluid for optics to skin.

R. Messerschmidt, Method for non-invasive blood analyte measurement with improved optical interface, U.S. Pat. No. 5,655,530 (Aug. 12, 1997), and R. Messerschmidt Method for non-invasive blood analyte measurement with improved optical interface, U.S. Pat. No. 5,823,951 (Oct. 20, 1998) describe an index-matching medium for use between a sensor probe and the skin surface. The index-matching medium is a composition containing both perfluorocarbons and chlorofluorocarbons.

M. Robinson, R. Messerschmidt, Method for non-invasive blood analyte measurement with improved optical interface, U.S. Pat. No. 6,152,876 (Nov. 28, 2000) and M. Rohrscheib, C. Gardner, M. Robinson, Method and apparatus for non-invasive blood analyte measurement with fluid compartment equilibration, U.S. Pat. No. 6,240,306 (May 29, 2001) describe an index-matching medium to improve the interface between the sensor probe and skin surface during spectroscopic analysis. The index-matching medium is preferably a composition containing chlorofluorocarbons with optional added perfluorocarbons.

T. Blank, G. Acosta, M. Mattu, S. Monfre, Fiber optic probe guide placement guide, U.S. Pat. No. 6,415,167 (Jul. 2, 2002) describe a coupling fluid of one or more perfluoro compounds where a quantity of the coupling fluid is placed at an interface of the optical probe and measurement site. Perfluoro compounds do not have the toxicity associated with chlorofluorocarbons.

M. Makarewicz, M. Mattu, T. Blank, G. Acosta, E. Handy, W. Hay, T. Stippick, B. Richie, Method and apparatus for minimizing spectral interference due to within and between sample variations during in-situ spectral sampling of tissue, U.S. patent application Ser. No. 09/954,856 (filed Sep. 17, 2001) describe a temperature and pressure controlled sample interface. The means of pressure control are a set of supports for the sample that control the natural position of the sample probe relative to the sample.

Positioning

E. Ashibe, Measuring condition setting jig, measuring condition setting method and biological measuring system, U.S. Pat. No. 6,381,489, Apr. 30, 2002 describes a measurement condition setting fixture secured to a measurement site, such as a living body, prior to measurement. At time of measurement, a light irradiating section and light receiving section of a measuring optical system are attached to the setting fixture to attach the measurement site to the optical system.

J. Röper, D. Böcker, System and method for the determination of tissue properties, U.S. Pat. No. 5,879,373 (Mar. 9, 1999) describe a device for reproducibly attaching a measuring device to a tissue surface.

J. Griffith, P. Cooper, T. Barker, Method and apparatus for non-invasive blood glucose sensing, U.S. Pat. No. 6,088,605 (Jul. 11, 2000) describe an analyzer with a patient forearm interface in which the forearm of the patient is moved in an incremental manner along the longitudinal axis of the patient's forearm. Spectra collected at incremental distances are averaged to take into account variations in the biological components of the skin. Between measurements rollers are used to raise the arm, move the arm relative to the apparatus and lower the arm by disengaging a solenoid causing the skin lifting mechanism to lower the arm into a new contact with the sensor head.

T. Blank, G. Acosta, M. Mattu, S. Monfre, Fiber optic probe placement guide, U.S. Pat. No. 6,415,167 (Jul. 2, 2002) describe a coupling fluid and the use of a guide in conjunction with a noninvasive glucose concentration analyzer in order to increase precision of the location of the sampled tissue site resulting in increased accuracy and precision in noninvasive glucose concentration estimations.

T. Blank, G. Acosta, M. Mattu, M. Makarewicz, S. Monfre, A. Lorenz, T. Ruchti, Optical sampling interface system for in-vivo measurement of tissue, world patent publication no. WO 2003/105664 (filed Jun. 11, 2003) describe an optical sampling interface system that includes an optical probe placement guide, a means for stabilizing the sampled tissue, and an optical coupler for repeatedly sampling a tissue measurement site in-vivo.

Clearly, there exists a need for controlling optical based sampling methods to minimize collection of specularly reflected light, for minimizing collection of stray light, to control the load applied by the sample probe to the measurement site as a function of time, and for minimizing sampling related changes to a deformable sample. For optical sampling of a deformable object, it would be desirable to provide a method and apparatus that automatically reduces the effects of non-contact and excessive contact of the sample during sampling.

SUMMARY OF THE INVENTION

The invention relates generally to a probe interface method and apparatus for use in conjunction with an optically based noninvasive analyzer. More particularly, an algorithm controls a sample probe position and attitude relative to a skin sample site during sampling.

DETAILED DESCRIPTION OF THE INVENTION

The invention comprises a noninvasive analyzer sampling module. Preferably the sample module controls position and/or attitude of a sample probe tip relative to a sample site. Optionally, the sample probe is controlled by an algorithm to minimally contact a sample site, tangentially contact a sample site and/or to controllably displace a tissue sample relative to the nominal plane of the sample tissue surface.

A key source of error in a noninvasive analyte property determination, such as a glucose concentration determination, is related to probe design and patient interface, as opposed to the spectrograph unit or algorithm design. A key parameter to control is the applied force or pressure applied by the sample probe to the interrogated tissue sample site. A force and/or displacement controlled sample interface aids generation of reproducible sample spectra used in conjunction with a noninvasive analyzer and algorithm to create acceptable reproducibility.

Preferably, a tip of a sample probe head of a sample module is controlled by an algorithm along a normal-to-skin-axis. Preferably, the sample probe head is positioned in terms of 3-D location in the x-, y-, and z-axes and is attitude orientated in terms of pitch, yaw, and roll. Further, attitude of the probe head is preferably orientated prior to contact of the sample probe head with the tissue sample using remote indicators, such as feedback from capacitance, optical, or electrical sensors.

Figure 1:
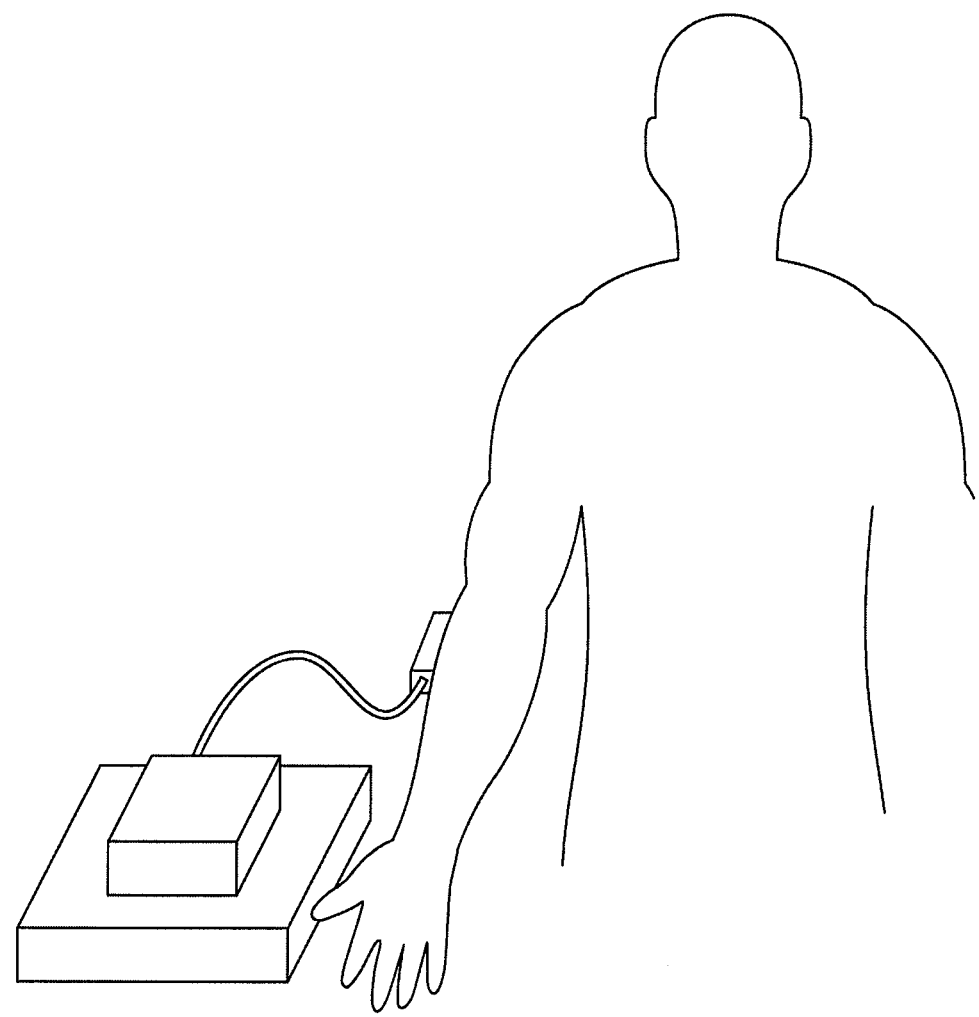
FIG. 1 illustrates an analyzer interfacing with a human body.

Referring now to FIG. 1, an analyzer 10 is illustrated interfacing with a human body. The analyzer, described infra, interfaces with any skin surface of the human body.

Coordinate System

Herein, positioning and attitude are defined. Positioning is defined using a x-, y-, and z-axes coordinate system relative to a given body part. A relative x-, y-, z-axes coordinate system is used to define a sample probe position relative to a sample site. The x-axis is defined along the length of a body part and the y-axis is defined across the body part. As an illustrative example using a sample site on the forearm, the x-axis runs between the elbow and the wrist and the y-axis runs across the axis of the forearm. Similarly, for a sample site on a digit of the hand, the x-axis runs between the base and tip of the digit and the y-axis runs across the digit. The z-axis is aligned with gravity and is perpendicular to the plane defined by the x- and y-axis. Further, the orientation of the sample probe relative to the sample site is defined in terms of attitude. Attitude is the state of roll, yaw, and pitch. Roll is rotation of a plane about the x-axis, pitch is rotation of a plane about the y-axis, and yaw is the rotation of a plane about the z-axis. Tilt is used to describe both roll and pitch.

Normal-to-skin-axis

Figure 2A:
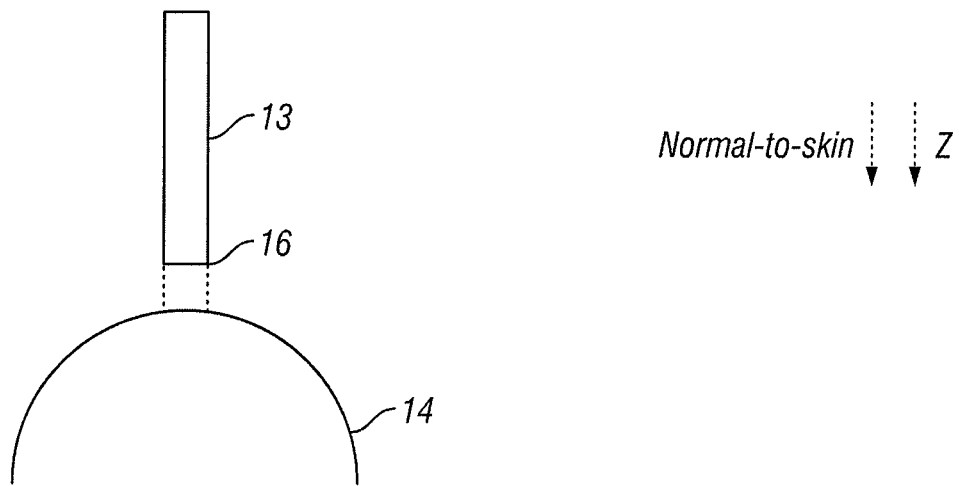
FIG. 2 illustrates a sample probe (A) moving along a z-axis and (B-C) moving along a normal-to-skin-axis.
Figure 2B:
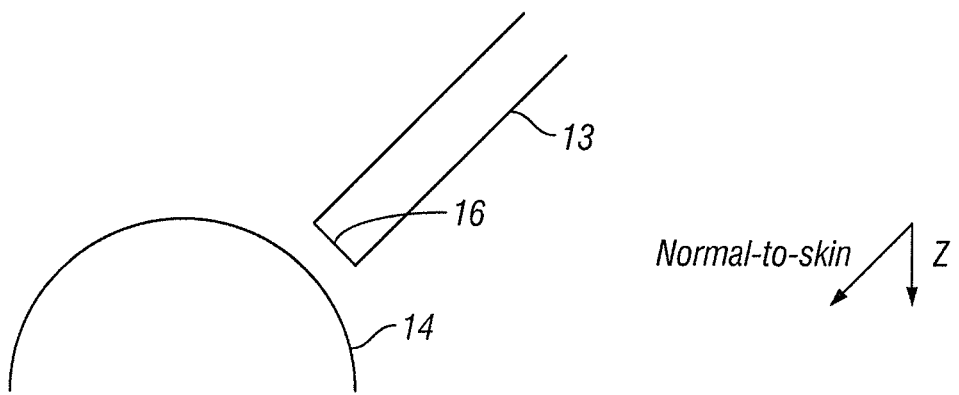
Figure 2C:
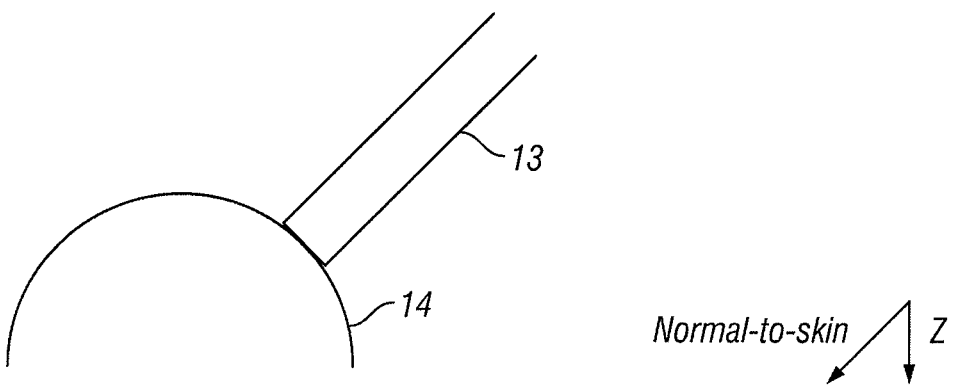

Position and attitude describe the sample probe tip surface relative to a sample site. Referring now to FIG. 2, both z-axis and normal-to-skin-axis movement of a sample probe relative to a sample site are illustrated. In FIG. 2A, a sample probe 13 having a sample probe tip 16 is illustrated relative to a skin sample 14. The skin sample 14 is illustrated with a greatly magnified surface curvature for ease of illustration and to emphasizing the importance of the localized curvature of the skin sample 14 surface. The sample probe 13 is moved from a position not in contact with the skin sample 14 as illustrated by the solid line. As illustrated by the dashed line, the sample probe tip is moved into contact with the sample 14 by moving the sample probe 14 along the z-axis. In this case, where the sample probe has no tilt relative to a sample point on the skin sample 14, the z-axis is also the normal-to-skin-axis. In FIG. 2B, the sample probe 13 is tilted relative to the sample point on the skin sample, where tilt is rotation of the sample probe through at least one of roll and pitch. Comparing FIGS. 2B and 2C, the sample probe 13 is observed to be brought to the skin sample 14 by moving the sample probe 13 along a normal-to-skin-axis. Notably, the normal-to-skin axis for the sample probe for the sample 14 illustrated in FIGS. 2B and 2C is not the same as movement along the z-axis as illustrated in FIG. 2A.

When the sample probe has tilt, movement of the sample probe along a normal-to-skin-axis has advantages as opposed to moving the sample probe along the z-axis. When the tilted sample is brought to the skin surface along the normal-to-skin-axis, the sample probe interacts with the skin with minimal energy. For example, shearing forces are minimized when the sample probe is brought to the sample site along the normal-to-skin-axis. In stark contrast, when the tilted sample probe is brought to the skin surface along the z-axis, a shearing force is applied to the skin. Similarly, the normal-to-skin-axis movement of the sample probe minimizes stress and strain on the sample site. As discussed, supra, the reduction of stress and strain on the sample site reduces spectrally observed interferences that degraded optical analyte property estimation, such as noninvasive glucose concentration determination. Further, movement of the sample probe along the normal-to-skin axis results in:

minimal application of force to the sample site to achieve sample probe/tissue sample contact;
minimal displacement of the pliable tissue sample when sample probe/tissue sample contact is achieved; and
a reduction or elimination of detected specularly reflected light off of the skin sample site surface with sample probe/tissue sample contact is achieved.

Preferably, the sample probe is brought to the sample site in terms of position and attitude using automated sample probe movement.

Instrumentation

Figure 3:
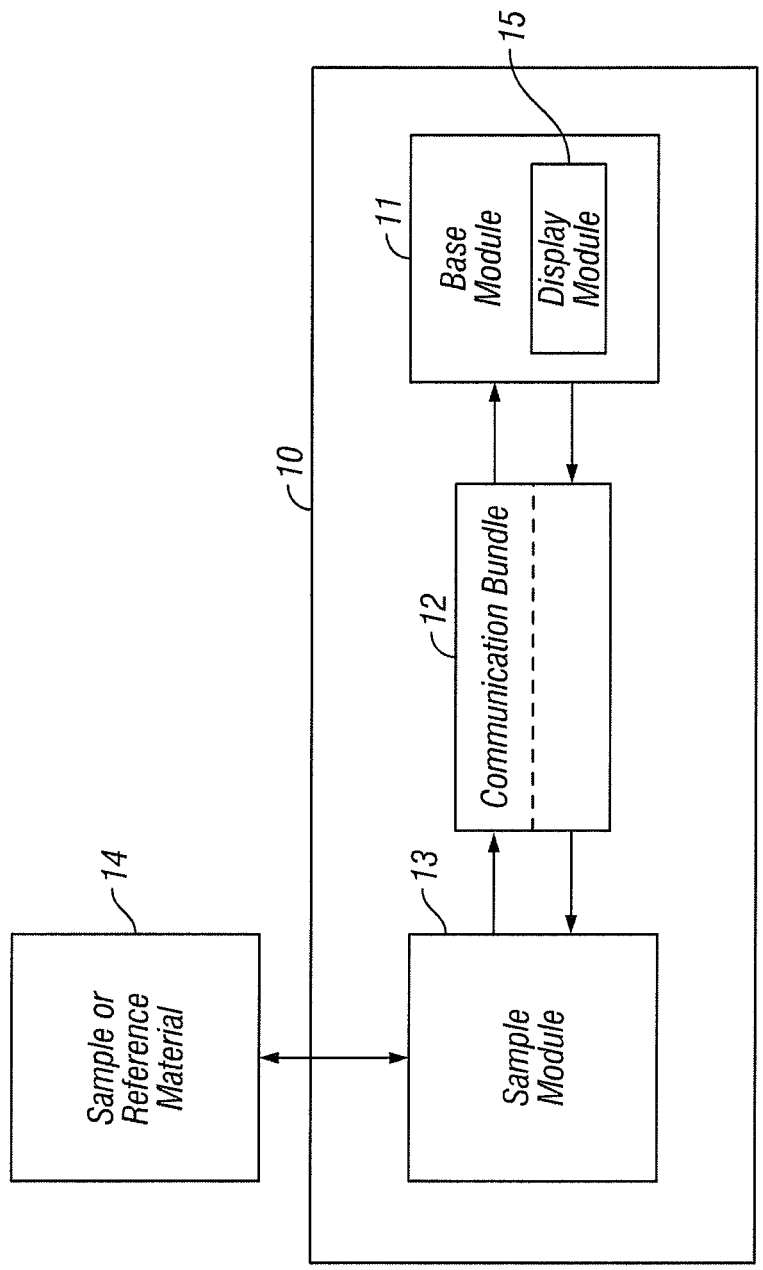
FIG. 3 illustrates a noninvasive analyzer including a base module, a communication bundle, and a sample module that is controlled by an algorithm, according to the invention.

Referring now to FIG. 3, an analyzer is illustrated. The analyzer 10 includes at least a source, illumination optics, collection optics, a detector, and an analysis algorithm. The analyzer 10 optionally includes a base module 11, communication bundle 12, and sample module 13. The base module has a display module. The analyzer components are optionally separated into separate housing units or are integrated into a single unit, such as a handheld unit. Preferably, a source is integrated into either the base module or the sample module. In a first case, the source element is integrated into the base module and the communication bundle carries the incident optical energy to the sample. In a second preferred case, the source element is integrated into the sample module. In both cases, photons are directed toward the tissue sample via a sample probe that is part of the sample module and the photonic signal collected from the sample by the sampling module is carried to a detector, typically in the base module, via the communication bundle. In an example of a noninvasive glucose concentration analyzer, the analyzer detects signals from a range of about 1100 to 1900 nm or about 1200 to 1800 nm.

Preferably, a signal processing means results in a control signal that is transferred from the base module via the communication bundle back to the sampling module. The communicated control signal is used to control the movement, such a position and attitude of the sample probe relative to the tissue sample or reference material.

Tissue Stress/Strain

The controller optionally moves the sample probe so as to make minimal, proximate, and/or controlled contact with a sample to control stress and/or strain on the tissue, which is often detrimental to a noninvasive analyte property determination. Strain is the elongation of material under load. Stress is a force that produces strain on a physical body. Strain is the deformation of a physical body under the action of applied force. In order for an elongated material to have strain there must be resistance to stretching. For example, an elongated spring has strain characterized by percent elongation, such as percent increase in length.

Skin contains constituents, such as collagen, that have spring-like properties. That is, elongation causes an increase in potential energy of the skin. Strain induced stress changes optical properties of skin, such as absorbance and scattering. Therefore, it is undesirable to make optical spectroscopy measurements on skin with various stress states. Stressed skin also causes fluid movements that are not reversible on a short timescale. The most precise optical measurements would therefore be conducted on skin in the natural strain state, such as minimally or non-stretched stretched skin. Skin is stretched or elongated by applying loads to skin along any of the x-, y-, and z-axes. Controlled contact reduces stress and strain on the sample. Reducing stress and strain on the sample results in more precise sampling and more accurate and precise glucose concentration estimations.

An example of using light to measure a physical property, such as contact, stress, and/or strain, in tissue is provided. Incident photons are directed at a sample and a portion of the photons returning from the sample are collected and detected. The detected photons are detected at various times, such as when no stress is applied to the tissue and when stress is applied to the tissue. For example, measurements are made when a sample probe is not yet in contact with the tissue and at various times when the sample probe is in contact with the tissue, such as immediately upon contact and with varying displacement of the sample probe into the tissue, such as within 0.5, 1, 2, 5, or 10 seconds from time of contact of the sample probe with the tissue. The displacement into the tissue is optionally at a controlled or variable rate. The collected light is used to determine properties. One exemplary property is establishing contact of the sample probe with the tissue. A second exemplary property is strain. The inventors determined that different frequencies of light are indicative of different forms of stress/strain. For example, in regions of high water absorbance, such as about 1450 nm, the absorbance is indicative of water movement. Additional regions, such as those about 1290 nm, are indicative of a dermal stretch. The time constant of the response for water movement versus dermal stretch is not the same. The more fluid water movement occurs approximately twenty percent faster than the dermal stretch. The two time constants allow interpretation of the tissue state from the resultant signal. For example, the interior or subsurface hydration state is inferred from the signal. For example, a ratio of responses at high absorbance regions and low absorbance regions, such as about 1450 and 1290 nm, is made at one or more times during a measurement period. Changes in the ratio are indicative of hydration. Optionally, data collection routines are varied depending upon the determined state of the tissue. For example, the probing tissue displacement is varied with change in hydration. The strain measurement is optionally made with either a targeting system or measurement system. The tissue state probe describe herein is optionally used in conjunction with a dynamic probe, described infra.

Actuator/Controller

A controller controls the movement of one or more sample probes of the targeting and/or measuring system via one or more actuators. An actuator moves the sample probe relative to the tissue sample. One or more actuators are used to control the position and/or attitude of the sample probe. The actuators preferably acquire feedback control signals from the measurement site or analyzer. The controller optionally uses an intelligent system for locating the sample site and/or for determining surface morphology. Controlled elements include any of the x-, y-, and z-axes positions of sampling along with pitch, yaw, and/or roll of the sample probe. Also optionally controlled are periods of light launch, intensity of light launch, depth of focus, and surface temperature. Several examples signal generation used with the controller and actuator follow.

In a first example, the controller hunts in the x- and y-axes for a spectral signature.

In a second example, the controller moves a sample probe via the actuator toward or away from the sample along the z-axis. The controller optionally uses feedback from a targeting system, from the measurement system, or from an outside sensor in a closed-loop mechanism for deciding on targeting probe movement and for sample probe movement.

In a third example, the controller optimizes a multivariate response, such as response due to chemical features or physical features. Examples of chemical features include blood/tissue constituents, such as water, protein, collagen, elastin, and fat. Examples of physical features include temperature, pressure, and tissue strain. Combinations of features are used to determine features, such as specular reflectance. For example, specular reflectance is a physical feature optionally measured with a chemical signature, such as water absorbance bands centered at about 1450, 1900, or 2600 nm.

In a fourth example, the controller uses signals acquired from the sample probe, such as capacitance sensors to determine distance between the sample probe and the tissue sample. For instance, the distance or relative distance between the sample probe tip and the sample site is determined. Due to the inverse relationship between capacitance and distance, the sensitivity to distance between the sample site and the sample probe increases as the distance between the sample and probe decreases. Using this metric, the sample probe is brought into close proximity to the sample site without displacing the sample site. Capacitance sensors, as used herein, are readily used to place the sample probe tip with a distance of less than about 0.5, 0.3, and preferably 0.1 millimeter to the sample site. A plurality of capacitance sensors on the sample probe head are used to determine distance of each portion of the sample probe tip from the skin sample site. The attitude of the sample probe head is adjusted so that the plane of the sample probe tip is brought down the normal-to-skin axis in a manner that the center of the sample probe tip contacts the sample site first. For instance, feedback from multiple capacitance sensors place along the along x- and/or y-axes is optionally used to adjust or control tilt of the sample probe tip. Preferably, the attitude adjustment of the sample probe tip is performed prior to the sample probe making contact with the skin tissue. Capacitance sensors are further described in U.S. patent application Ser. No. 11/625,752 filed Jan. 22, 2007, which is incorporated herein in its entirety by this reference thereto.

In a fifth example, one or more contact sensors are used to determine contact of the sample probe tip with the sample site. Acceptable optical contact is ascertained on the basis of one or more contact sensors, which surround or are in close proximity to the detection optic. As the sample probe is placed in mechanical contact with the skin tissue, a signal is generated by the contact sensor which indicates a contact event. For example, a conductive contact is detected when the signal changes from its mean level by an amount greater than two times the standard deviation of the noise. An electrical contact sensor provides a rise in current as an indication that proximate contact between said sample probe tip and the sample site is established. Upon initial contact with one section of a sample probe tip, a sample is collected or the tip is backed off from the sample site and attitude adjusted to be tangential to the center of the sample site. Contact sensors are further described in U.S. provisional patent application No. 60/864,375 filed Nov. 3, 2006, which is incorporated herein in its entirety by this reference thereto.

In a sixth example, the controller controls elements resulting in pathlength and/or depth of penetration variation. For example, the controller controls an adjustable iris in the sample probe for control of radial spread of incident light, a rotating wheel, a focusable backreflector, or an incident optic controlling position and angle of incident light.

Preferably, two or more of the above described sensor response are used cooperatively in controlling the sample probe position and/or attitude of the analyzer relative to the sample. For example, the various sensor systems are used in control of the motion of the sample probe at different distances between a tip of the sample probe and the tissue sample. In a particular example, a target/vision system is used to find a tissue sample site to move the analyzer probe head toward, a capacitive sensor system is used to orient the tilt of the probe head to nominally match that of the skin surface at the sample site, the capacitive sensor is further used in positioning the sample probe head close to the sample site, and a conductive sensor system is used in fine positioning of the tip of the sample probe headed to distances of less than a tenth of a millimeter and preferably about a hundredth of a millimeter from the tissue sample site.

The actuator/controller move the sample probe tip so that the optical and physical effect of displacement of tissue by the sample probe head prior to or during sampling is minimized.

Effect of Displacement on Tissue Spectra

Figure 4:
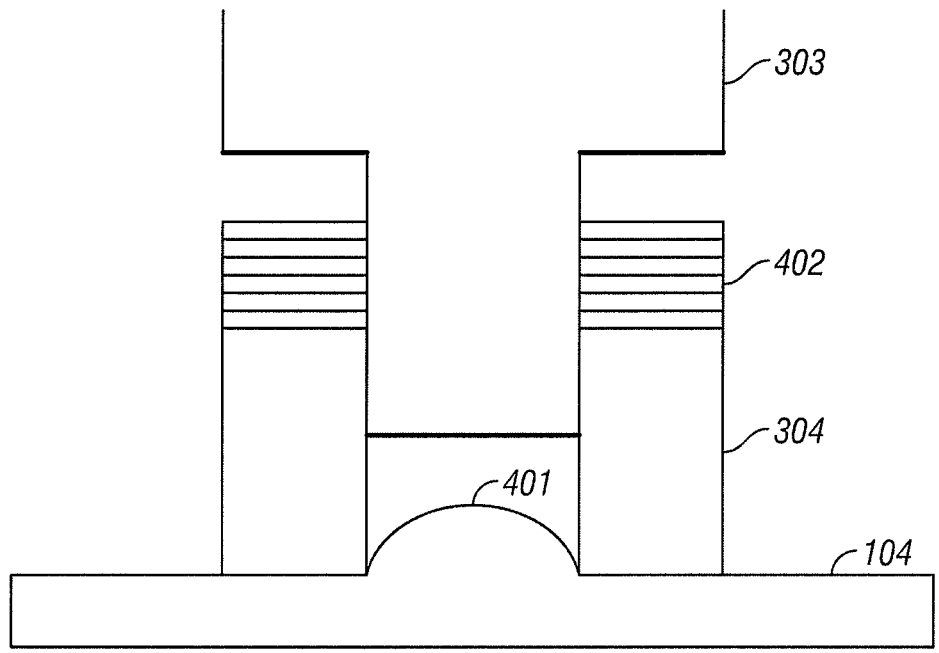
FIG. 4 illustrates a movable sample probe.
Figure 4:
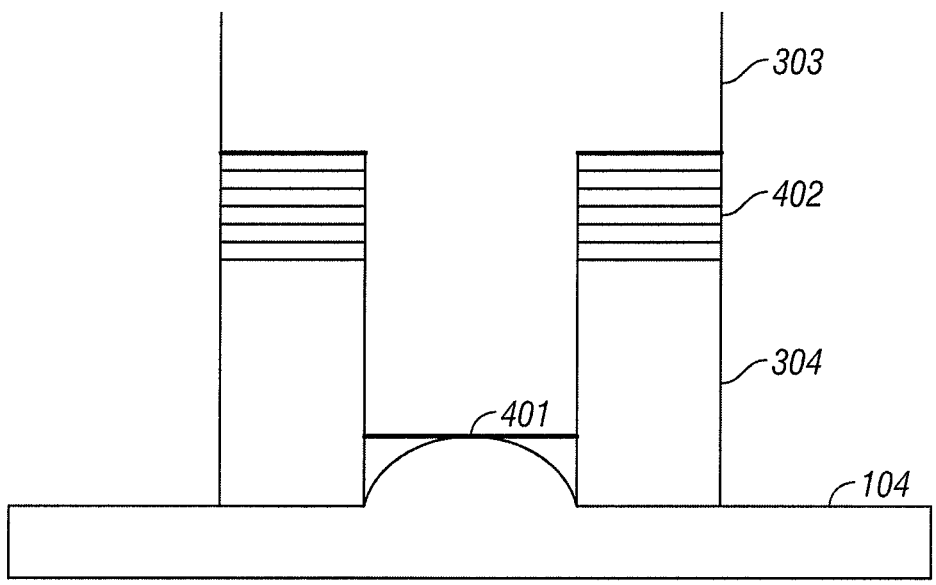

In the following experiment, the effect on noninvasive spectra of displacement of a sample probe on a tissue sample is demonstrated. A movable sample probe contained in the sample module is presented in a first position not in contact with the sample in time 1 of FIG. 4. In this example, the sample probe is guided to the sample location with an optional guide element described in T. Blank, G. Acosta, M. Mattu, S. Monfre, Fiber optic probe guide placement guide, U.S. Pat. No. 6,415,167 (Jul. 2, 2002), which is herein incorporated in its entirety by reference. The guide element is replaceably attached to the sample site. The attachment of the guide to the sample site results in formation of a meniscus of skin in the opening of the guide. The meniscus is typically a convex bulge of tissue from the nominal plane of the skin tissue but is flat or concave in some individuals such as older people or those with less collagen density at the sample site. The size of the meniscus is subject dependent, varies on a given subject from day-to-day, and varies on a subject within a day. A series of spacers are placed on top of the guide that sterically provide a stop to the sample probe as the sample probe moves down the z-axis, perpendicular to the skin surface, toward the tissue sample. As individual spacers are removed, the sample probe initiates contact with the sample. Removal of additional spacers results in probe displacement of the deformable tissue sample.

Figure 5A:
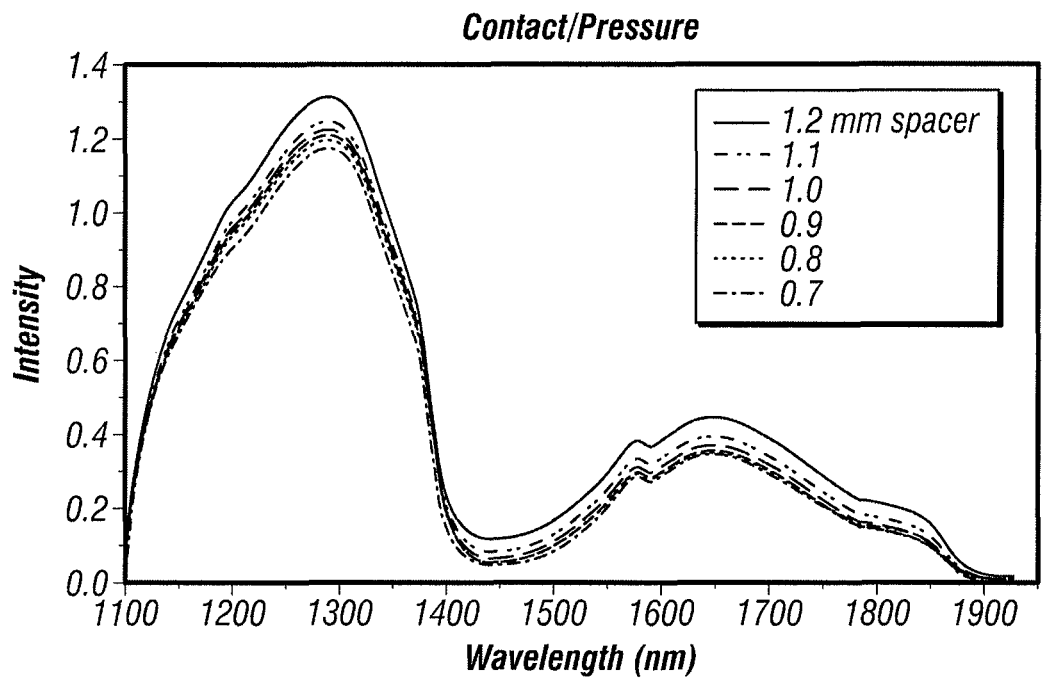
FIG. 5 demonstrates contact pressure results in spectral variation.
Figure 5B:
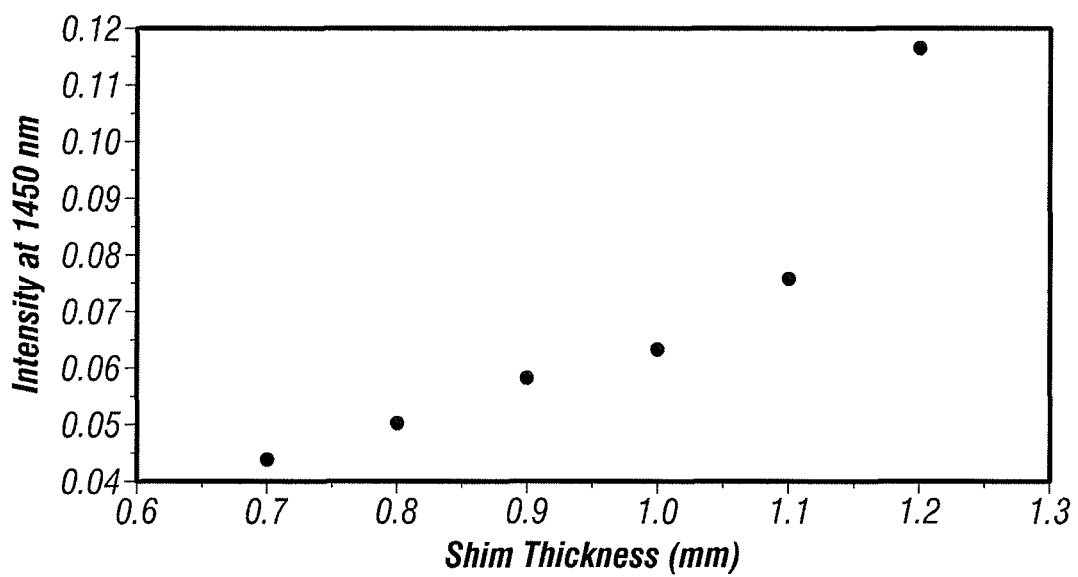

Spectra are collected with subsequent removal of the steric stops described supra. The resulting single beam spectra from 1100 to 1930 nm collected with a 1.2, 1.1, 1.0, 0.9, 0.8, and 0.7 mm spacer are presented in FIG. 5A. It is the relative movement of the sample probe along the z-axis relative to the tissue sample that is important as opposed to the size of the spacers. The observed intensity decreases as spacers are removed and contact followed by displacement of the tissue results. Two dominant spectral features are observed: the light of the second overtone region from 1100 to 1450 nm and the light of the first overtone region from 1450 to 1900 nm. The decrease in light intensity in these regions is due to chemical and physical effects including large water absorbance bands at 1450 and 1930 nm described infra. The decrease in intensity at 1450 nm is further analyzed in FIG. 5B. The observed intensity of 0.116 volts with a 1.2 mm spacer indicates that the sample probe has not yet made contact with the tissue sample. The large drop in observed intensity with a decrease in sample probe height of $1/10^{th}$ of a millimeter to 1.1 mm indicates that contact with the skin is established. This is confirmed by observing that at all wavelengths the intensity decrease is most significant with this single change in spacer height and indicates that specularly reflected light is significantly reduced and that the resulting spectra are now dominated by the absorbance and scattering nature of the tissue sample. This pedestal effect is described in S. Malin U.S. Pat. No. 6,040,578, supra, and is herein incorporated in its entirety by reference. Subsequent removal of spacers results in a further displacement of the tissue sample by the sample probe. Increasing displacement of the tissue sample by the sample probe result in changes in the observed intensity of spectral bands associated with chemical and physical features.

Figure 6:
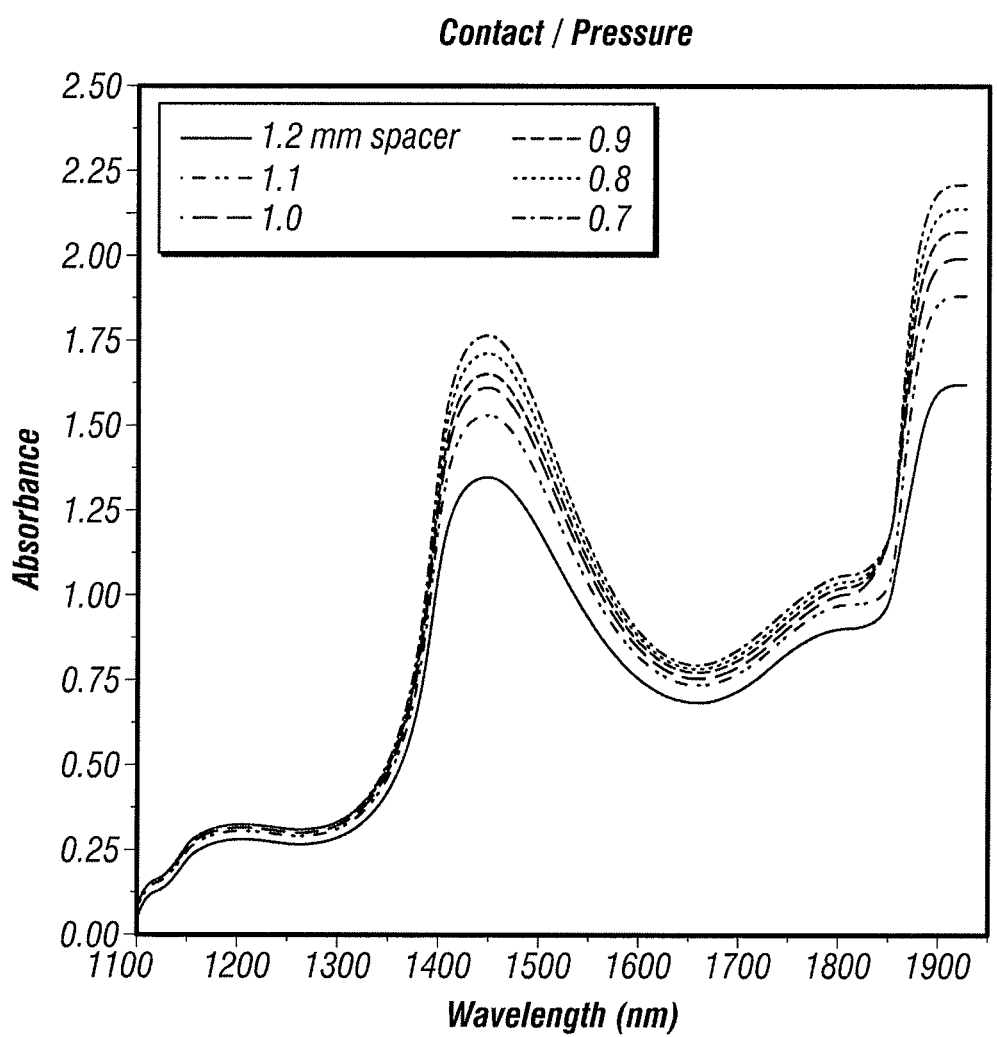
FIG. 6 demonstrates contact pressure results in spectral variation.
Figure 7:
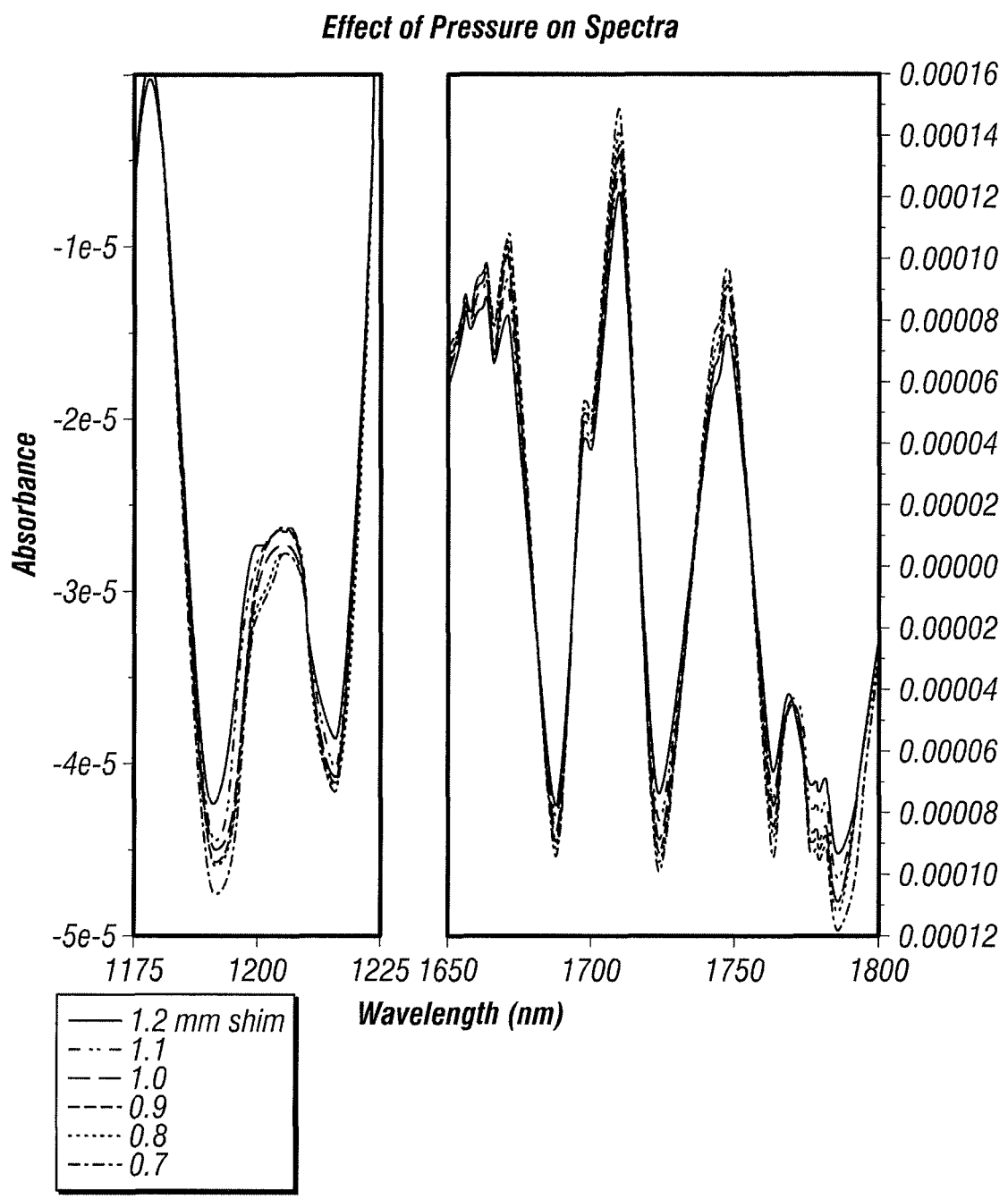
FIG. 7 demonstrates contact pressure results in spectral variation.

The single beam spectra collected as a function of displacement of the tissue sample are subsequently converted into absorbance spectra with use of an intensity reference spectrum and are presented in FIG. 6. The resulting absorbance spectra reveal chemical and physical features of the sample. Two large water absorbance bands are observed centered at 1450 and 1930 nm. Smaller fat and protein absorbance bands are observed in the first and second overtone spectral regions. Scattering effects are observed throughout the spectrum but are most prevalent in the higher energy region of the spectra. The sample collected with the 1.2 mm spacer that resulted in insufficient contact of the sample probe with the tissue sample results in artificially low absorbance across the spectrum due to the collection of spectrally reflected light into the collection optics of the sample probe. In order to enhance the chemical features observed in the first and second overtone spectral windows, the spectra were first smoothed across time and subsequently smoothed across wavelengths with a Savitsky-Golay 13 point second derivative. The resulting spectra are presented in FIG. 7. The second derivative reduces the scattering characteristics and allow the observation of the chemical features. The spectral minima observed at 1152, 1687, and 1720 nm are dominated by the absorbance of water, protein, and fat, respectively.

Figure 8:
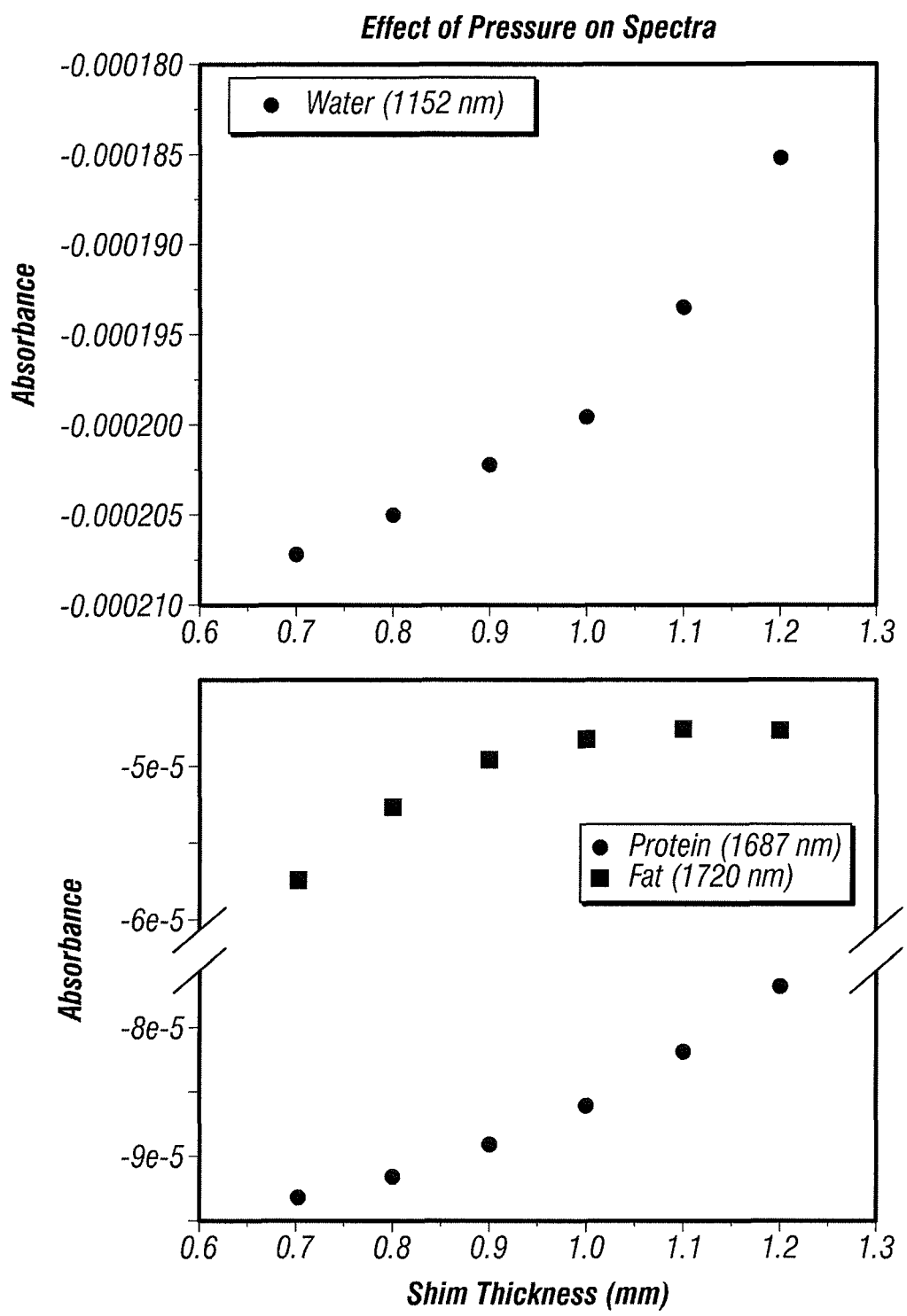
FIG. 8 demonstrates contact pressure results in spectral variation.

The change in absorbance of the water, protein, and fat spectral features is plotted as a function of displacement in FIG. 8. In this example, the absorbance of all three chemical features is observed to decrease with increasing displacement of the sample probe into the tissue sample. The dependence of the absorbance of the individual chemical and physical features as a function of tissue displacement is dependent upon a range of factors. The factors include: the physical dimension of the sample probe tip interfacing with the tissue sample, the dimension of the aperture in the guide, the chemical composition of the tissue sample, the rate of displacement of the sample probe into the tissue, and a historesis effect of previous contact of an outside object on the sample site.

The displacement of the tissue sample by the sample probe results in compression of the sample site. The displacement results in a number of changes including at least one of: a change in the localized water concentration as fluid is displaced, a change in the localized concentration of chemicals that are not displaced such as collagen, and a correlated change in the localized scattering concentration. In addition, physical features of the sample site are changed. These changes include at least one of: a compression of the epidermal ridge, compression of the dermal papilla, compression of blood capillaries, deformation of skin collagen, and the relative movement of components embedded in skin.

Figure 9:
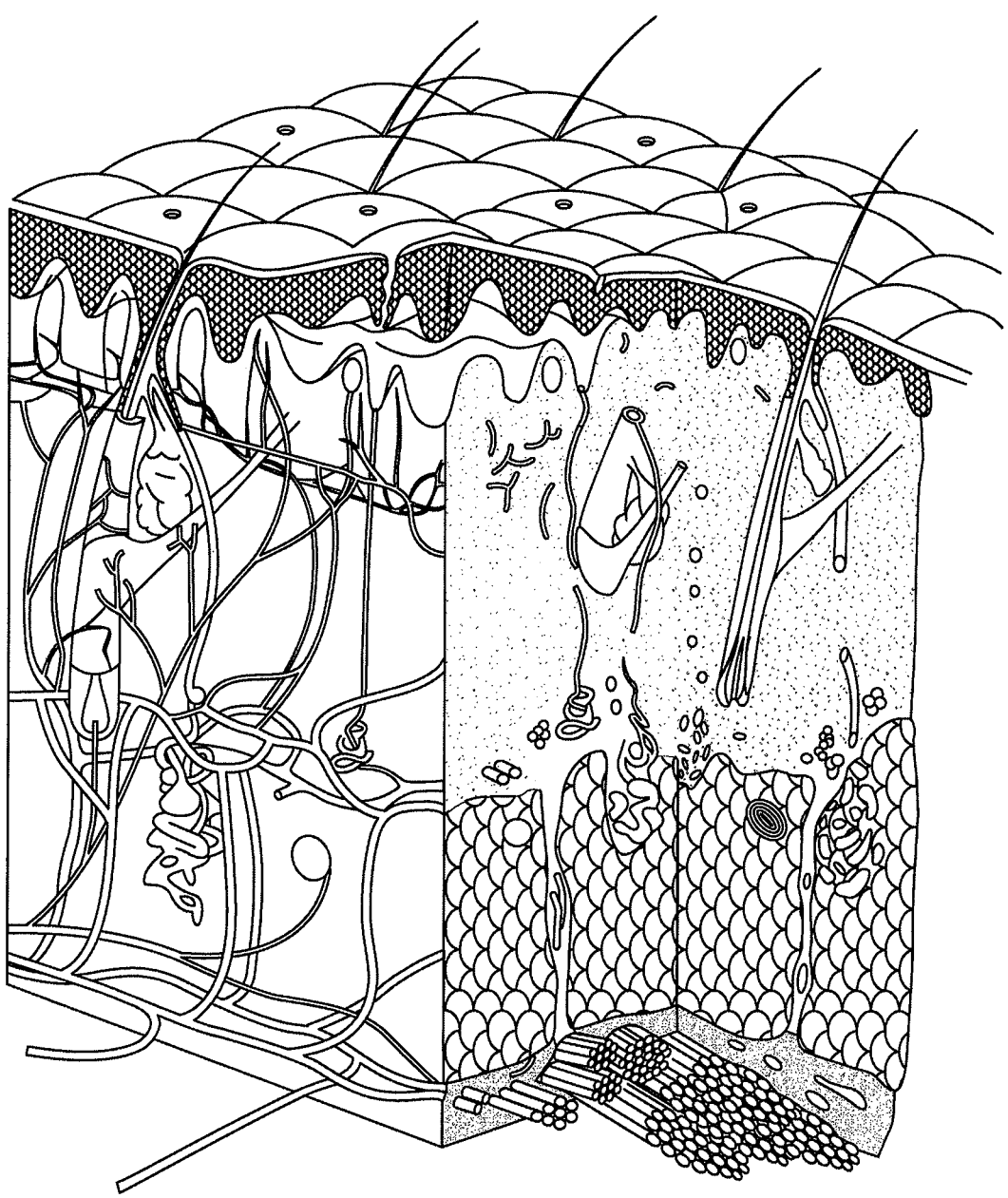
FIG. 9 illustrates skin constituents.

In this example, chemical and physical changes are observed with displacement of the sample probe into the tissue sample. Specific chemical features at three wavelengths are described. However, the displacement of tissue is demonstrated by this example to effect the spectra over a wide range of wavelengths from 1100 to 1930 nm. Additional spectral data shows these pressure effects to be present in at least the infrared region extending out to 2500 nm. Further, the displacement effects are described for a few particular chemical and physical structures. The displacement of tissue also effects a number of additional skin chemical, physical, and structural features presented in FIG. 9.

Preferred Embodiments

In a preferred embodiment, the sample probe is a part of the sample module and the sample probe is controlled by an algorithm along the normal-to-skin-axis. Preferably, the sample probe head is positioned in terms of 3-D location in the x-, y-, and z-axes and is attitude orientated in terms of pitch, yaw, and roll.

Figure 10:
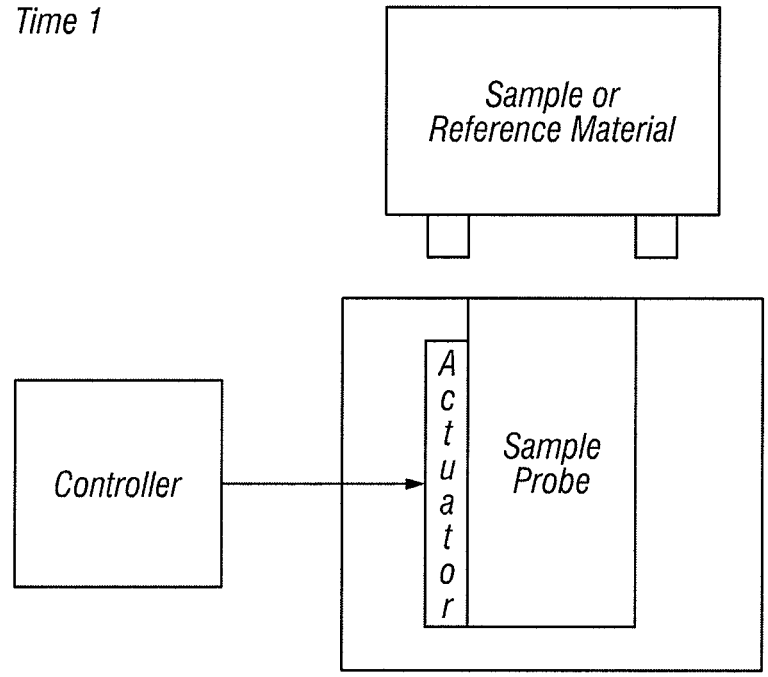
FIG. 10 illustrates a controller/actuator controlled sample probe.
Figure 10:
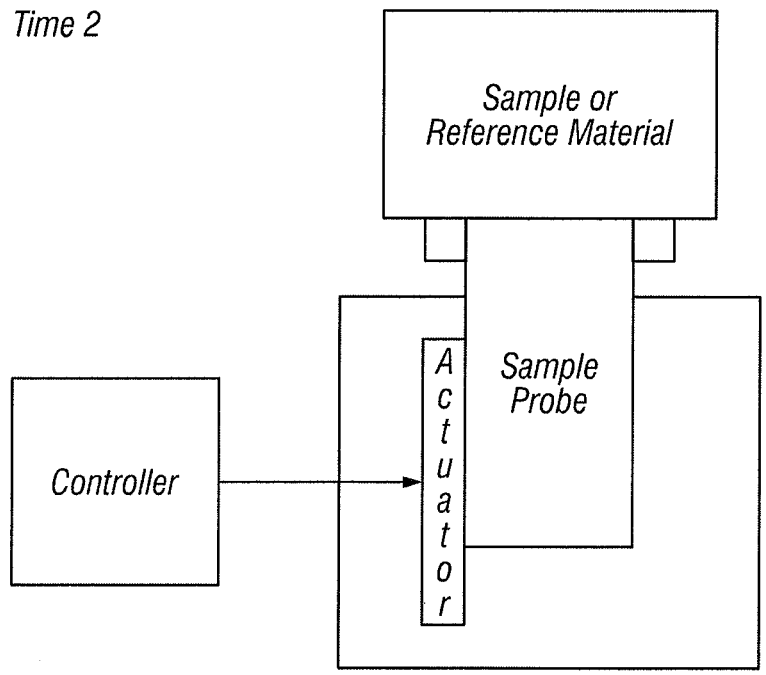

A schematic presentation of the sample module is presented in FIG. 10. The sample module includes an actuator and a sample probe. The actuator is driven by a controller. The controller sends the control signal from the algorithm to the sample module actuator via a communication bundle. The actuator subsequently moves the sample probe relative to the tissue sample site. The sample probe is controlled along the z-axis from a position of no contact, to a position of tissue sample contact, and optionally to a position of minimal tissue sample displacement. The sample probe is presented in FIG. 10 at a first and second period of time with the first time period presenting the sample probe when it is not in contact with the sample site. The second time period presents the sample probe with minimal displacement of the sample tissue.

Figure 11:
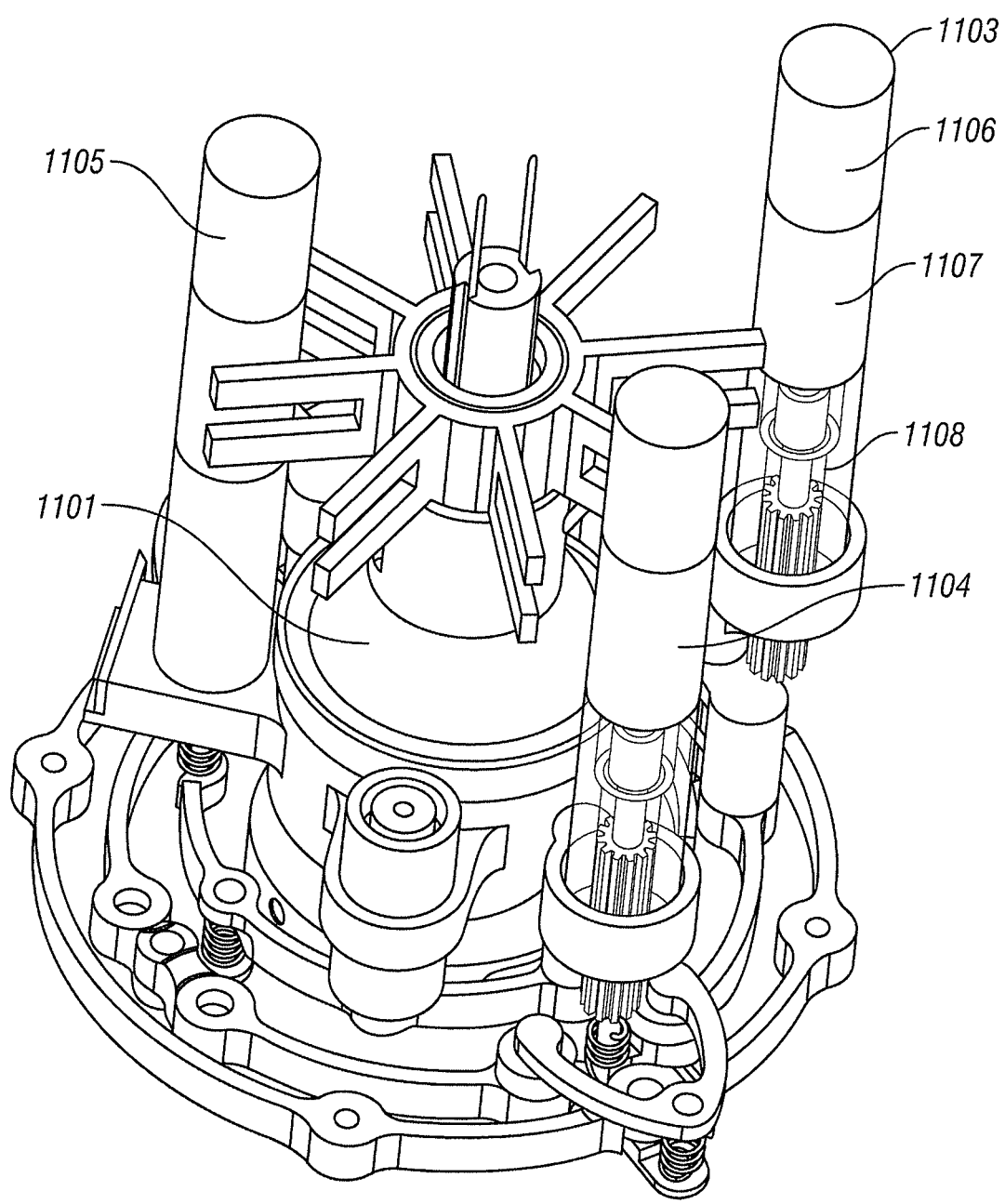
FIG. 11 illustrates an attitude controller for a sample probe.

In another embodiment of the invention, a mechanical system for adjusting attitude is affixed to a sample module or sample probe. Referring now to FIG. 11, a sample module is presented with the outside cover removed for clarity. A reflector 1101 reflects light from a source toward the sample. Heat from the source is dissipated through a heat sink 1102. In this example, three drive mechanisms are used. Each illustrated drive mechanism contains a motor 1106, gear box 1107, and bushing in a spline shaft 1108, though any drive means capable of adjusting roll, pitch, or position along the normal-to-skin-axis is suitable. The first motor assembly 1103 adjusts pitch, the second motor assembly 1104 adjusts roll, and the third motor assembly 1105 moves the tip of the sample probe along a normal-to-skin axis.

Figure 12:
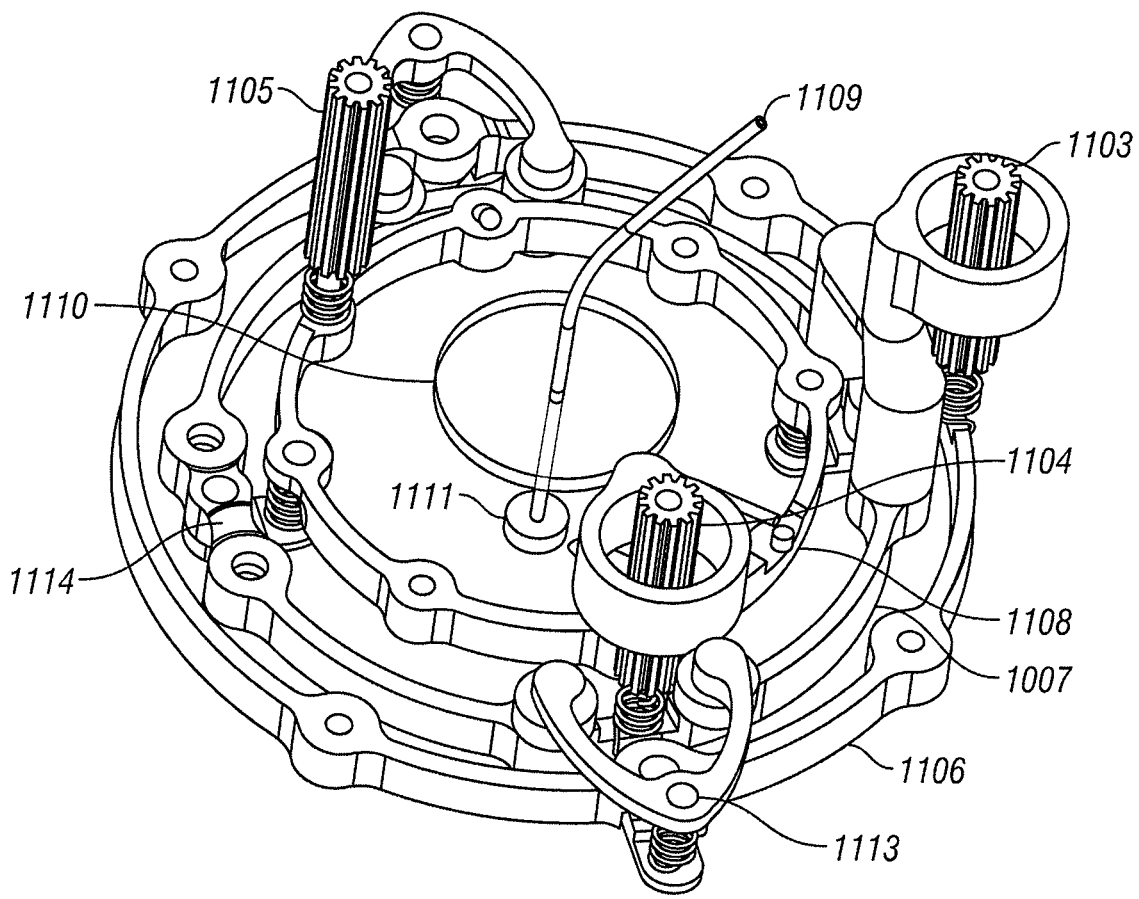
FIG. 12 illustrates an attitude controller for a sample probe.

Referring now to FIG. 12, items of the assembly of FIG. 11 are removed to further expose internal elements. The spline shaft internals of the three motor assemblies 1103-1105 are illustrated. The pictured design has three concentric rings 1106-1108 for controlling attitude, though other mechanical systems are usable. Movement of the first motor assembly 1103 operates through a pivot point 1113 to move the second concentric ring 1107 to control pitch of the sample probe tip. Movement of the second motor 1104 operates through a second pivot point 1114 to move the third concentric ring 1108 to control roll of the sample probe tip. Movement of the third motor 1105 controls movement of the sample probe tip along the normal-to-skin-axis.

Also illustrated in FIG. 12 are a collection optic 1109, first illumination optic 1110, and second illumination optic 1111. Within the sample module, the collection optic is surrounded by a light barrier to prevent source light from penetrating into the collection optic. For example, within the sample probe a metal sheath surrounds the collection fiber optic. The first optic 1110 operates as any of a longpass filter, shortpass filter, or bandpass filter to remove spectral regions of undesirable photons. For example, the first optic 1110 removes infrared heat at wavelengths longer than about 1900 or 2500 nm. As a second example, the first optic comprises silicon and removes light at wavelengths shorter than about 1100 nm. The first optic does not contact the skin sample 14. The second optic 1111 proximately contacts the skin sample 14 during analyzer use. The second optic preferably contains a hole through which the collection optic 1109 penetrates to make proximate contact with the skin surface. The second optic 1111 mechanically supports the tip of the collection optic 1109. Extending radially about the collection optic 1109 is a spacer placed between the collection optic 1109 and the second optic 1111.

Figure 13:
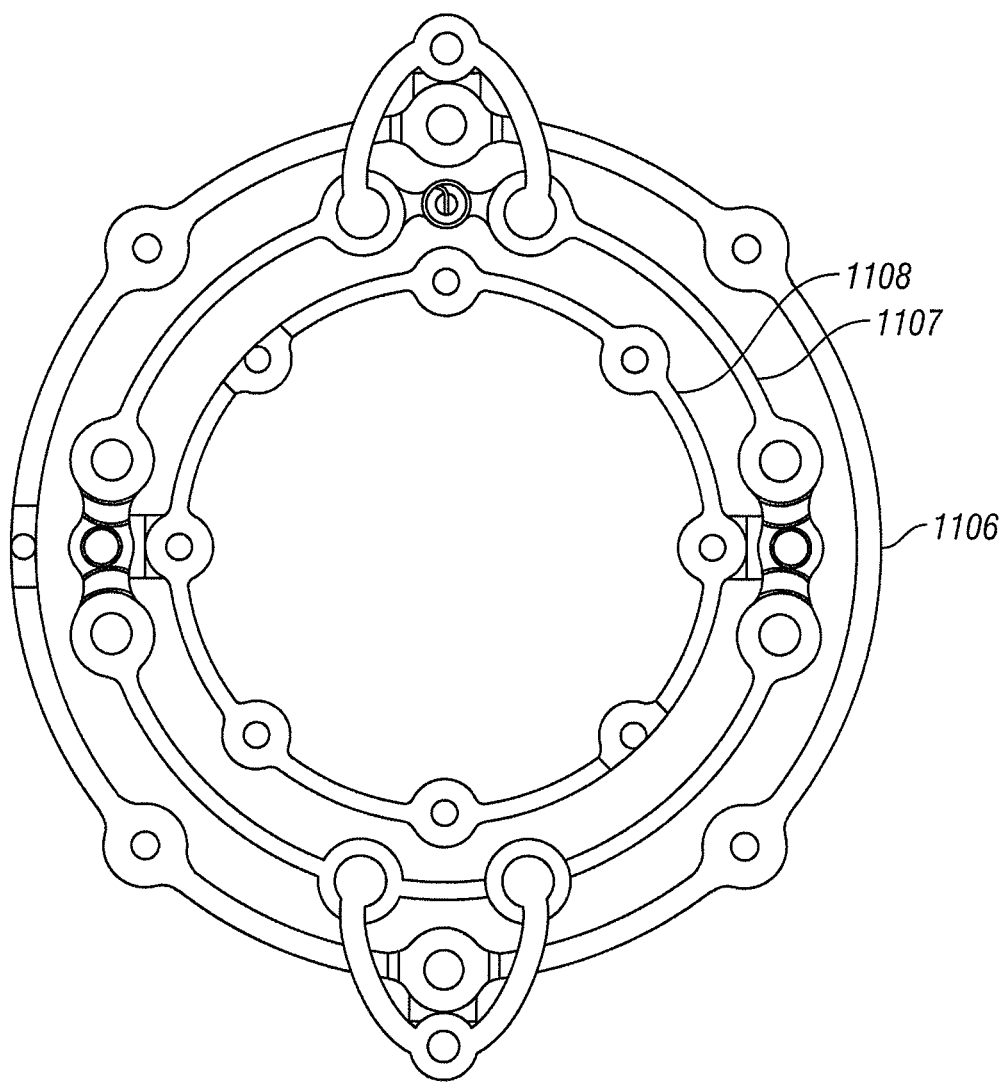
FIG. 13 illustrates an attitude controller for a sample probe in a non-tilt state.
Figure 13:
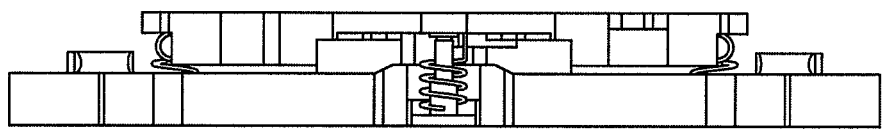
Figure 14:
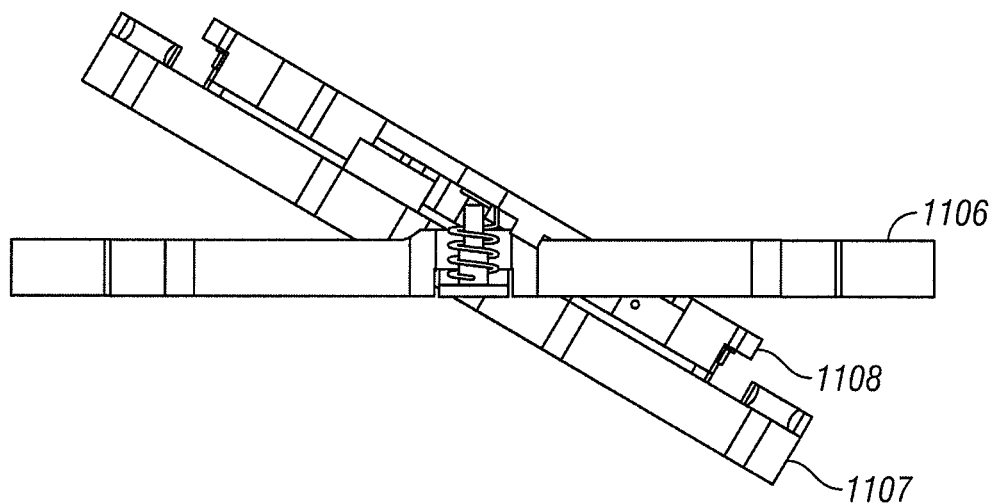
FIG. 14 illustrates an attitude controller for a sample probe in a pitched state.
Figure 15:
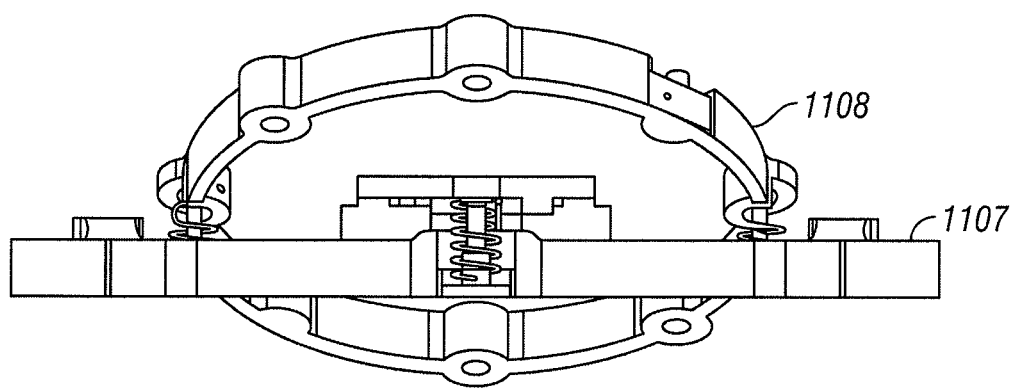
FIG. 15 illustrates an attitude controller for a sample probe in a rolled state.

Tilt is illustrated in FIGS. 13-15. Referring now to FIG. 13, the three concentric rings 1106-1108 of FIG. 12 are illustrated as a top down view and as a side view when the system is in a state of no pitch or roll. Referring now to FIG. 14, movement of the lead screw of the first motor 1103 results in pitch of the second ring 1107 and third ring 1108 relative to the first concentric ring 1106. Referring now to FIG. 15, movement of the lead screw of the second motor 1104 results in roll of the third ring 1108 relative to the second concentric ring 1107.

In another embodiment, attitude control of the sample probe tip relative to a curved sample site or tissue site in terms of roll, pitch, and/or yaw is controlled using a set of linear drives in combination with ball pivots and slides to alter attitude of a mounting plate. The linear drives, or alternatively drive motors, can also be used to control motion of the sample probe tip along a z-axis or an axis normal to the surface of a tissue site.

Tissue Displacement Control

Displacement of the tissue sample by the sample probe results in changes in noninvasive spectra. Displacement of the sample tissue is related to pressure applied to the sample tissue. However, as the tissue is deformed the return force applied by the tissue sample to the sample probe varies. Therefore, it is preferable to discuss that sample/tissue interaction in terms of displacement instead of pressure.

Displacement of the tissue sample by the sample probe is preferably controlled between an insufficient and excessive displacement or pressure. Insufficient contact of the sample probe with the tissue sample is detrimental. The surface of the skin tends to be rough and irregular. Insufficient contact results in a surface reflection. Contact between the sample probe and the tissue sample minimizes air pockets and reduces optical interface reflections that contain no useful information. Contact pressure must be high enough to provide good optical transmission of source illumination into the capillary layer where the analytical signal exists while minimizing reflections from the surface of the skin that manifest as noise. Excessive displacement of the tissue sample by the sample probe is detrimental. The primary region of interest for measurement of blood borne analytes is the capillary bed of the dermis region, which is approximately 0.1 to 0.4 mm beneath the surface. The capillary bed is a compressible region and is sensitive to pressure, torque, and deformation effects. The accurate representation of blood borne analytes that are used by the body through time, such as glucose, relies on the transport of blood to and from the capillary bed, so it is not preferable to restrict this fluid movement. Therefore, contact pressure should not be so high as to excessively restrict or to partially restrict for an extended period of time flow of blood and interstitial fluids to the sampled tissue region.

In the foregoing discussion, the preferred embodiment of the invention is for the determination of a glucose concentration. Additional analytes for concentration or threshold determination are those found in the body including: water, protein, fat and/or lipids, blood urea nitrogen (BUN), both therapeutic and illicit drugs, and alcohol.

Those skilled in the art will recognize that the present invention may be manifested in a variety of forms other than the specific embodiments described and contemplated herein. Departures in form and detail may be made without departing from the spirit and scope of the present invention. Accordingly, the invention should only be limited by the Claims included below.

The invention claimed is:

1. A noninvasive spectroscopic analyzer configured to determine an analyte property from a sample site of a body part, comprising:
   a sample probe having a sample probe tip;
   a controller for controlling attitude of said sample probe tip relative to localized curvature of the sample site based on an input;
   a first motor operating through a first pivot point positioned on a first concentric ring to move a second concentric ring to control pitch of said sample probe tip; and
   a second motor operating through a second pivot point positioned on the second concentric ring to move a third concentric ring to control roll of said sample probe tip; and
   wherein the controller adjusts the attitude including at least pitch and roll of said sample probe relative to the localized curvature of the sample site by controlling the first and second motors;
   wherein the input is configured to receive an input signal providing said controller with information about said attitude of said sample probe tip relative to the sample site.

2. The noninvasive spectroscopic analyzer of claim 1, wherein attitude of said sample probe tip relative to the sample site is defined in terms of an x-, y-, and z-axis coordinate system, wherein said x-axis is defined along a length of said body part, wherein said y-axis is defined across said body part, and wherein said z-axis is normal to a plane formed by said x- and y-axes.

3. The noninvasive spectroscopic analyzer of claim 2, wherein said controller controls said attitude of said sample probe tip along all of said x-, y-, and z-axes.

4. The noninvasive spectroscopic analyzer of claim 2, wherein said controller controls said attitude of said sample probe tip along a normal-to-sample site axis, wherein said normal-to-sample site axis is not said z-axis.

5. The noninvasive spectroscopic analyzer of claim 2, wherein pitch comprises rotation of said sample probe tip about said y-axis, wherein roll comprises rotation of said sample probe tip about said x-axis.

6. The noninvasive spectroscopic analyzer of claim 2, further comprising: a third motor for controlling movement of said sample probe tip along a normal-to-skin-axis, wherein said normal-to-skin axis is tangential to a plane defined by said x- and y-axes and is not aligned with an axis corresponding to that of a force attributable to gravity.

7. The noninvasive spectroscopic analyzer of claim 6, wherein the third motor is positioned at a periphery of the third concentric ring to move the sample probe tip along the normal-to-skin-axis.

8. The noninvasive spectroscopic analyzer of claim 1, wherein said input is further configured to receive said input signal comprising a plurality of capacitance signals, wherein each of said plurality of capacitance signals provides information on a distance between a localized section of said sample probe tip and the sample site.

9. The noninvasive spectroscopic analyzer of claim 1, wherein said input signal comprises a conductive contact signal, wherein said conductive contact signal changes in current as an indication that proximate contact between said sample probe tip and the sample site is established.

10. The noninvasive spectroscopic analyzer of claim 1, further comprising: means for adjusting position of said sample probe tip relative to the sample site, wherein said controller adjusts pitch and roll of said sample probe tip and, thereafter, said means for adjusting moves said sample probe tip along a normal-to-skin axis, wherein said normal-to-skin axis is not aligned with an axis corresponding to that of a force attributable to gravity.

11. The noninvasive spectroscopic analyzer of claim 1, wherein the first motor is positioned at a periphery of the first concentric ring to move the second concentric ring.

12. The noninvasive spectroscopic analyzer of claim 1, wherein the second motor is positioned at a periphery of the second concentric ring to move the third concentric ring.

13. A method for analyte property determination from a sample site of a body part, comprising the steps of:
    collecting a spectrum with a noninvasive analyzer comprising: a sample probe having a sample probe tip; and a controller; and
    controlling attitude including at least pitch and roll of said sample probe tip about a first concentric ring with said controller relative to localized curvature of the sample site based on an input by:
        moving a second concentric ring relative to the first concentric ring to control pitch of said sample probe tip with a first motor; and
        moving a third concentric ring relative to the second concentric ring to control roll of said sample probe tip with a second motor;
    wherein the input is configured to receive an input signal providing said controller with information about said attitude of said sample probe tip relative to the sample site.

14. The method of claim 13, further comprising the step of: positioning said sample probe tip at an attitude relative to the sample site, wherein said attitude is defined in terms of an x-, y-, and z-axis coordinate system, wherein said x-axis is defined along the length of a body part, wherein said y-axis is defined across said body part, wherein said z-axis is normal to a plane formed by said x- and y-axes.

15. The method of claim 14, further comprising the step of: said controller controlling attitude of said sample probe tip along all of said x-, y-, and z-axes.

16. The method of claim 14, wherein said z-axis comprises a normal-to-sample site axis, wherein said z-axis does not align with an axis corresponding to that of a force attributable to gravity.

17. The method of claim 14, wherein pitch comprises rotation of said sample probe tip about said y-axis, and wherein roll comprises rotation of said sample probe tip about said x-axis.

18. The method of claim 13, wherein said input signal comprises a plurality of capacitance signals; and further comprising the step of each of said plurality of capacitance signals providing information on a distance between a localized section of said sample probe tip and the sample site.

19. The method of claim 13, wherein said input signal comprises a conductive contact signal; and further comprising the step of said conductive contact signal rising in current as an indication that proximate contact between said sample probe tip and the sample site is established.

20. The method of claim 13, further comprising the step of: adjusting position of said sample probe tip relative to the sample site, wherein said controller adjusts pitch and roll of said sample probe tip and, thereafter, moves said sample probe tip along a normal-to-skin axis, wherein said normal-to-skin axis is not aligned with an axis corresponding to that of a force attributable to gravity.

21. The method of claim 13, further comprising the step of: a third motor controlling movement of said sample probe tip along an axis that is normal to said sample site axis, wherein said normal to skin said sample site axis is not aligned with an axis corresponding to that of a force attributable to gravity.

22. The method of claim 13, further comprising the step of: generating a glucose concentration from said spectrum, wherein said spectrum comprises signals at wavelengths from about 1200 to above 1800 nm.

23. The method of claim 13, wherein the first motor positioned at a periphery of the first concentric ring is configured to move the second concentric ring, and wherein the second motor positioned at a periphery of the second concentric ring is configured to move the third concentric ring.

* * * * *

UNITED STATES PATENT AND TRADEMARK OFFICE
CERTIFICATE OF CORRECTION

| | | |
|---|---|---|
| PATENT NO. | : 8,868,147 B2 | Page 1 of 1 |
| APPLICATION NO. | : 12/125017 | |
| DATED | : October 21, 2014 | |
| INVENTOR(S) | : Timothy W. Stippick et al. | |

It is certified that error appears in the above-identified patent and that said Letters Patent is hereby corrected as shown below:

Title Page, Related U.S. Application Data (63), lines 5-6, Change "which is a continuation-in-part of application No. PCT/US2007/083497, filed on Nov. 2, 2007." to --and is a continuation-in-part of application No. PCT/US2007/083497, filed on Nov. 2, 2007.--

Signed and Sealed this
Seventeenth Day of February, 2015

Michelle K. Lee
*Deputy Director of the United States Patent and Trademark Office*